(12) United States Patent
Matsubara

(10) Patent No.: US 11,480,780 B2
(45) Date of Patent: Oct. 25, 2022

(54) OBSERVATION DEVICE, OBSERVATION METHOD, AND OBSERVATION DEVICE CONTROL PROGRAM

(71) Applicant: FUJIFILM CORPORATION, Tokyo (JP)

(72) Inventor: Kenta Matsubara, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 274 days.

(21) Appl. No.: 15/931,596

(22) Filed: May 14, 2020

(65) Prior Publication Data
US 2020/0271914 A1 Aug. 27, 2020

Related U.S. Application Data

(63) Continuation of application No. PCT/JP2018/040387, filed on Oct. 30, 2018.

(30) Foreign Application Priority Data

Nov. 17, 2017 (JP) .............................. JP2017-221445

(51) Int. Cl.
G02B 21/36 (2006.01)
G02B 21/00 (2006.01)
G01N 1/28 (2006.01)

(52) U.S. Cl.
CPC ......... *G02B 21/361* (2013.01); *G02B 21/006* (2013.01); *G02B 21/0032* (2013.01); *G02B 21/0036* (2013.01); *G01N 1/28* (2013.01)

(58) Field of Classification Search
None
See application file for complete search history.

(56) References Cited

U.S. PATENT DOCUMENTS

2003/0193600 A1* 10/2003 Kitamura ......... H04N 5/232945
348/E5.037
2006/0000962 A1* 1/2006 Imabayashi .......... G02B 21/245
250/201.2
(Continued)

FOREIGN PATENT DOCUMENTS

JP 2008-292216 A 12/2008
JP 2009-25349 A 2/2009
(Continued)

OTHER PUBLICATIONS

International Search Report issued in International Application No. PCT/JP2018/040387 dated Feb. 5, 2019.
(Continued)

Primary Examiner — Talha M Nawaz
(74) Attorney, Agent, or Firm — Solaris Intellectual Property Group, PLLC

(57) ABSTRACT

By moving at least one of a culture container having a plurality of wells or an imaging optical system that forms an image of an observation target in each of the wells, an observation position in the culture container is scanned to observe the observation target. In a case where an auto-focus control for each observation position is performed, a start timing of the auto-focus control for each observation position is switched on the basis of a boundary portion between the adjacent wells in a scanning direction of the observation position.

34 Claims, 13 Drawing Sheets

(56) References Cited

U.S. PATENT DOCUMENTS

| 2010/0103254 | A1  |         | 4/2010  | Okamoto |                      |
|--------------|-----|---------|---------|---------|----------------------|
| 2015/0130920 | A1  | *       | 5/2015  | Zou     | G02B 21/361          |
|              |     |         |         |         | 348/79               |
| 2015/0144699 | A1  | *       | 5/2015  | Sackett | G06K 7/10831         |
|              |     |         |         |         | 235/462.24           |
| 2016/0306153 | A1  |         | 10/2016 | Okamoto |                      |

FOREIGN PATENT DOCUMENTS

| JP | 2010-72017   | A  | 4/2010  |
|----|--------------|----|---------|
| JP | 2010-91739   | A  | 4/2010  |
| WO | 2009/025345  | A1 | 2/2009  |
| WO | 2013/165576  | A1 | 11/2013 |
| WO | 2018/061635  | A1 | 4/2018  |

OTHER PUBLICATIONS

Written Opinion of the ISA issued in International Application No. PCT/JP2018/040387 dated Feb. 5, 2019.
Extended European Search Report dated Dec. 16, 2020, issued in corresponding EP Patent Application No. 18878865.7.

* cited by examiner

OBSERVATION DEVICE, OBSERVATION METHOD, AND OBSERVATION DEVICE CONTROL PROGRAM

CROSS REFERENCE TO RELATED APPLICATIONS

The present application is a Continuation of PCT International Application No. PCT/JP2018/040387 filed on Oct. 30, 2018, which claims priority to Japanese Patent Application No. 2017-221445 filed on Nov. 17, 2017. Each of the above applications is hereby expressly incorporated by reference, in its entirety, into the present application.

BACKGROUND

Technical Field

The present disclosure relates to an observation device, an observation method, and an observation device control program for observing an entire image of an observation target by moving a container in which the observation target is contained with respect to an imaging optical system that forms an image of the observation target.

Related Art

In the related art, a method for capturing an image of a multipotential stem cell such as an embryonic stem (ES) cell or an induced pluripotent stem (iPS) cell, a differentiated and induced cell, or the like using a microscope or the like, and capturing a feature of the image to decide a differentiation state of the cell, or the like has been proposed.

The multipotential stem cell such as an ES cell or an iPS cell is able to be differentiated into cells of various tissues, and may be applied to regenerative medicine, development of medicines, explanation of diseases, or the like.

On the other hand, as described above, in a case where cells are imaged with a microscope, a technique for performing so-called tiling imaging has been proposed in order to acquire a high-magnification wide view image. Specifically, for example, a range of a culture container such as a well plate is scanned by an imaging optical system, and an image at each observation position is captured, and then, the images at the respective observation positions are combined.

In a case where such tiling imaging is performed, it has been proposed to obtain a high-quality image with less blur by performing an auto-focus control at each observation position in the culture container (see JP2010-072017A, JP2008-292216A, JP2009-025349A, or the like).

Here, as described above, in a case where the auto-focus control is performed in the above-mentioned tiling imaging, it is important to perform the auto-focus control at high speed and with high accuracy from the viewpoint of reducing an imaging time.

However, for example, in a case where a well plate having a plurality of wells is used as a culture container, the entire well plate is scanned by an imaging optical system, and the tiling imaging is performed while performing the auto-focus control for each observation position, the thickness of a bottom portion of each well varies from well to well due to a manufacturing error, or the like.

Accordingly, for example, in a case where the auto-focus control is performed by detecting a position of the bottom surface of the well (an observation target installation surface) to perform the auto-focus control, in a case where the thickness of the bottom portion differs greatly between adjacent wells, since the position of the bottom surface of the well differs greatly, there is a problem that the time for the auto-focus control becomes longer and the imaging time becomes longer.

SUMMARY OF THE INVENTION

The present disclosure has been made in view of the above problems, and has an object to provide an observation device and method, and an observation device control program capable of efficiently performing an auto-focus control and reducing the imaging time.

According to an aspect of the present disclosure, there is provided an observation device including: an imaging optical system having an imaging lens that forms an image of an observation target in a plurality of containers in which the observation target is contained; an imaging system having an imaging element that captures the image of the observation target formed by the imaging optical system; an operation section that performs at least one of a first operation of changing a focal length of the imaging optical system, a second operation of moving the imaging lens in an optical axis direction, a third operation of moving the imaging element in the optical axis direction, or a fourth operation of moving the container in the optical axis direction; a horizontal driving section that moves at least one of the container or the imaging optical system in a horizontal plane; a scanning controller that controls the horizontal driving section and moves at least one of the container or the imaging optical system to scan an observation position in the container; and an auto-focus controller that controls the operation section and performs an auto-focus control for each observation position, in which the auto-focus controller switches a start timing of the auto-focus control for each observation position, on the basis of a boundary portion between the adjacent containers in a scanning direction of the observation position.

According to the above aspect of the present disclosure, in the observation device, the operation section may perform a plurality of operations among the first operation, the second operation, the third operation, and the fourth operation.

According to another aspect of the present disclosure, there is provided an observation device including: an imaging optical system having an imaging lens that forms an image of an observation target in a plurality of containers in which the observation target is contained; an operation section that performs at least one of a first operation of changing a focal length of the imaging optical system, a second operation of moving the imaging lens in an optical axis direction, or a fourth operation of moving the container in the optical axis direction; a horizontal driving section that moves at least one of the container or the imaging optical system in a horizontal plane; a scanning controller that controls the horizontal driving section and moves at least one of the container or the imaging optical system to scan an observation position in the container; and an auto-focus controller that controls the operation section and performs an auto-focus control for each observation position, in which the auto-focus controller switches a start timing of the auto-focus control for each observation position, on the basis of a boundary portion between the adjacent containers in a scanning direction of the observation position.

According to the above aspect of the present disclosure, the operation section may perform a plurality of operations among the first operation, the second operation, and the fourth operation.

Further, according to the above aspects of the present disclosure, in the observation device, the imaging optical system may further include an objective lens that forms the image of the observation target in the container, and the first operation may include at least one of an operation of changing a focal length of the imaging lens or an operation of changing a focal length of the objective lens.

Further, according to the above aspects of the present disclosure, the observation device may further include a focal length changing optical system that changes the focal length of the imaging optical system, in which the imaging optical system may further include an objective lens that forms the image of the observation target in the container, and the first operation may include at least one of an operation of changing a focal length of the imaging lens, an operation of changing a focal length of the objective lens, or an operation of changing the focal length of the imaging optical system by the focal length changing optical system.

According to the above aspects of the present disclosure, in the observation device, the operation section may perform a fifth operation of moving the objective lens in the optical axis direction.

Further, according to the above aspects of the present disclosure, the observation device may further include a focal length changing optical system that changes the focal length of the imaging optical system, in which the first operation may include an operation of changing the focal length of the imaging optical system by the focal length changing optical system.

Further, according to the above aspects of the present disclosure, in the observation device, the imaging optical system may further include an objective lens that forms the image of the observation target in the container, and the operation section may perform a fifth operation of moving the objective lens in the optical axis direction.

According to the above aspects of the present disclosure, in the observation device, the auto-focus controller may start the auto-focus control of the observation position immediately after the boundary portion from a time point when the auto-focus control of the observation position immediately before the boundary portion is terminated until before the imaging optical system reaches the observation position immediately after the boundary portion.

According to the above aspects of the present disclosure, in the observation device, the auto-focus controller may start, for an observation position other than the observation position immediately after the boundary portion, the auto-focus control from a time point when the imaging optical system reaches the observation position.

Further, according to the above aspects of the present disclosure, in the observation device, a time for the auto-focus control of the observation position immediately after the boundary portion may be longer than a time for the auto-focus control of the observation position other than the observation position immediately after the boundary portion.

In addition, according to the above aspects of the present disclosure, the observation device may further include a detection section that precedently detects a vertical position of the container at the observation position before the imaging optical system reaches the observation position, in which the auto-focus controller may perform the auto-focus control for each observation position on the basis of a detection signal of the detection section.

Further, according to the above aspects of the present disclosure, in the observation device, the detection section may include at least two displacement sensors that are provided in parallel in the scanning direction with the imaging optical system being interposed therebetween, and the displacement sensor to be used may be switched according to a directional change of the scanning direction.

According to the above aspects of the present disclosure, in the observation device, the detection section may detect a boundary portion of the container.

Further, according to the above aspects of the present disclosure, in the observation device, the auto-focus controller may perform, in a case where the detection signal detected by the detection section is abnormal, for an observation position where the abnormal detection signal is detected, the auto-focus control based on the detection signals of the detection section for previous and next observation positions in the scanning direction of the observation position.

In addition, according to the above aspects of the present disclosure, the observation device may further include a storage unit that stores position information of a boundary portion of the container, in which the auto-focus controller may switches a start timing of the auto-focus control on the basis of the position information of the boundary portion stored in the storage unit.

Furthermore, according to the above aspects of the present disclosure, the container may be each well of a well plate.

According to still another aspect of the present disclosure, there is provided an observation method for moving at least one of a plurality of containers in which an observation target is contained, or an imaging optical system having an imaging lens that forms an image of the observation target in each of the containers, to scan each observation position in the container in an observation region of the imaging optical system and capture an image of the observation target imaged by the imaging optical system using an imaging element, including: a step of performing at least one of a first operation of changing a focal length of the imaging optical system, a second operation of moving the imaging lens in an optical axis direction, a third operation of moving the imaging element in the optical axis direction, or a fourth operation of moving the container in the optical axis direction; and a step of switching a start timing of an auto-focus control for each observation position, on the basis of a boundary portion between the adjacent containers in a scanning direction of the observation position.

According to still another aspect of the present disclosure, there is provided an observation method for moving at least one of a plurality of containers in which an observation target is contained, or an imaging optical system having an imaging lens that forms an image of the observation target in each of the containers, to scan each observation position in the container in an observation region of the imaging optical system, including: a step of performing at least one of a first operation of changing a focal length of the imaging optical system, a second operation of moving the imaging lens in an optical axis direction, or a fourth operation of moving the container in the optical axis direction; and a step of switching a start timing of an auto-focus control for each observation position, on the basis of a boundary portion between the adjacent containers in a scanning direction of the observation position.

According to still another aspect of the present disclosure, there is provided an observation device control program that causes a computer to execute an observation method for moving at least one of a plurality of containers in which an observation target is contained, or an imaging optical system having an imaging lens that forms an image of the observation target in each of the containers, to scan each observation position in the container in an observation region of the imaging optical system and capture an image of the observation target imaged by the imaging optical system using an imaging element, the program causing the computer to execute: a step of performing at least one of a first operation of changing a focal length of the imaging optical system, a second operation of moving the imaging lens in an optical axis direction, a third operation of moving the imaging element in the optical axis direction, or a fourth operation of moving the container in the optical axis direction; and a step of switching a start timing of an auto-focus control for each observation position, on the basis of a boundary portion between the adjacent containers in a scanning direction of the observation position.

According to still another aspect of the present disclosure, there is provided an observation device control program that causes a computer to execute an observation method for moving at least one of a plurality of containers in which an observation target is contained, or an imaging optical system having an imaging lens that forms an image of the observation target in each of the containers, to scan each observation position in the container in an observation region of the imaging optical system, the program causing the computer to execute: a step of performing at least one of a first operation of changing a focal length of the imaging optical system, a second operation of moving the imaging lens in an optical axis direction, or a fourth operation of moving the container in the optical axis direction; and a step of switching a start timing of an auto-focus control for each observation position, on the basis of a boundary portion between the adjacent containers in a scanning direction of the observation position.

According to still another aspect of the present disclosure, there is provided an observation device including: a memory that stores a command to be executed by a computer; and a processor configured to execute the stored command, in which the processor executes a process of moving at least one of a plurality of containers in which an observation target is contained, or an imaging optical system having an imaging lens that forms an image of the observation target in each of the containers, to scan each observation position in the container in an observation region of the imaging optical system and capture an image of the observation target imaged by the imaging optical system using an imaging element, in which the process includes: a step of performing at least one of a first operation of changing a focal length of the imaging optical system, a second operation of moving the imaging lens in an optical axis direction, a third operation of moving the imaging element in the optical axis direction, or a fourth operation of moving the container in the optical axis direction, and a step of switching a start timing of an auto-focus control for each observation position, on the basis of a boundary portion between the adjacent containers in a scanning direction of the observation position.

According to still another aspect of the present disclosure, there is provided an observation device including: a memory that stores a command to be executed by a computer; and a processor configured to execute the stored command, in which the processor executes a process of moving at least one of a plurality of containers in which an observation target is contained, or an imaging optical system having an imaging lens that forms an image of the observation target in each of the containers, to scan each observation position in the container in an observation region of the imaging optical system, in which the process includes: a step of performing at least one of a first operation of changing a focal length of the imaging optical system, a second operation of moving the imaging lens in an optical axis direction, or a fourth operation of moving the container in the optical axis direction, and a step of switching a start timing of an auto-focus control for each observation position, on the basis of a boundary portion between the adjacent containers in a scanning direction of the observation position.

According to the observation device and method, and the observation device control program of the above aspects of the present disclosure, by moving at least one of a plurality of containers in which an observation target is contained, or an imaging optical system having an objective lens that forms an image of the observation target in each of the containers, each observation position in the container is scanned and the observation target is observed. Further, by performing at least one of a first operation of changing a focal length of the imaging optical system, a second operation of moving the imaging lens in an optical axis direction, a third operation of moving the imaging element in the optical axis direction, or a fourth operation of moving the container in the optical axis direction, in a case where the auto-focus control for each observation position is performed, a start timing of an auto-focus control for each observation position is switched on the basis of a boundary portion between the adjacent containers in a scanning direction of the observation position. Accordingly, it is possible to more efficiently perform the auto-focus control, and reduce the imaging time.

According to the observation device and method, and the observation device control program of the above aspects of the present disclosure, by moving at least one of a plurality of containers in which an observation target is contained, or an imaging optical system having an imaging lens that forms an image of the observation target in each of the containers, each observation position in the container is scanned and the observation target is observed. Further, by performing at least one of a first operation of changing a focal length of the imaging optical system, a second operation of moving the imaging lens in an optical axis direction, or a fourth operation of moving the container in the optical axis direction, in a case where the auto-focus control for each observation position is performed, a start timing of an auto-focus control for each observation position is switched on the basis of a boundary portion between the adjacent containers in a scanning direction of the observation position. Accordingly, it is possible to more efficiently perform the auto-focus control, and reduce the imaging time.

BRIEF DESCRIPTION OF THE DRAWINGS

FIG. 14 is a diagram showing a position in a Z direction based on a detection signal detected by a detection section in a case where a bottom surface of a well has a flaw or the like.

DETAILED DESCRIPTION

Figure 1:
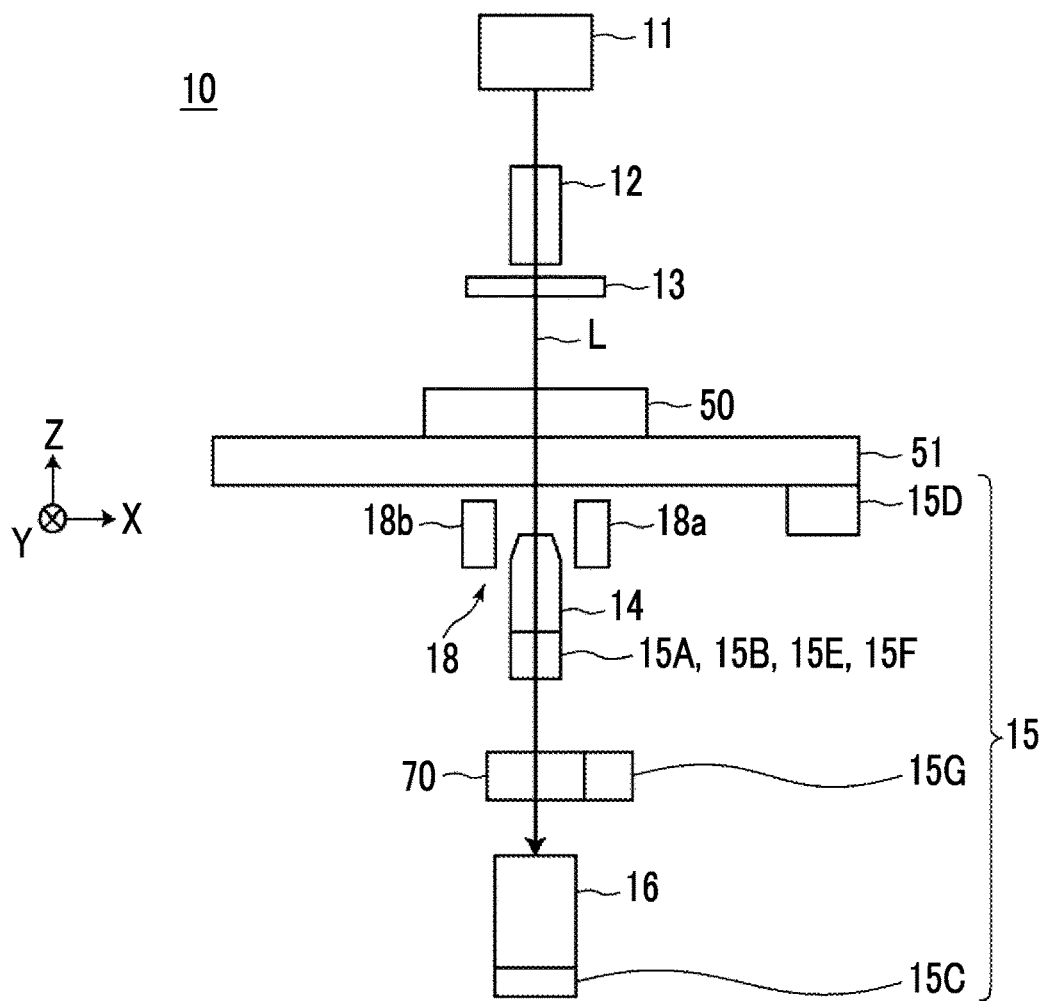
FIG. 1 is a diagram showing a schematic configuration of a microscope in a microscope observation system that uses an observation device according to an embodiment of the present disclosure.

Hereinafter, a microscope observation system that uses an observation device and an observation method according to an embodiment of the present disclosure will be described in detail with reference to the accompanying drawings. FIG. 1 is a diagram showing a schematic configuration of a microscope device 10 in a microscope observation system of the embodiment.

The microscope device 10 captures a phase difference image of a cultured cell that is an observation target. Specifically, as shown in FIG. 1, the microscope device 10 includes a white light source 11 that emits white light, a condenser lens 12, a slit plate 13, an imaging optical system 14, an operation section 15, an imaging element 16, and a detection section 18. Further, the microscope device 10 includes a focal length changing optical system 70.

The operation section 15 includes a first operation section 15A, a second operation section 15B, a third operation section 15C, a fourth operation section 15D, a fifth operation section 15E, a sixth operation section 15F, and a seventh operation section 15G Operations of the first to seventh operation sections 15A to 15G will be described later.

Figure 2:
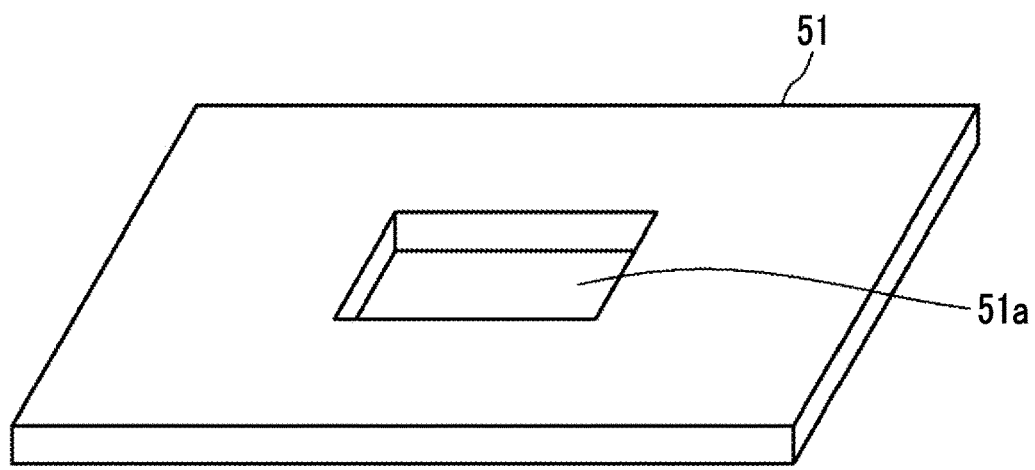
FIG. 2 is a perspective view showing a configuration of a stage.

Further, a stage 51 is provided between the slit plate 13, and the imaging optical system 14 and the detection section 18. A culture container 50 in which cells that are observation targets are contained is installed on the stage 51. FIG. 2 is a diagram showing an example of the stage 51. At the center of the stage 51, a rectangular opening 51a is formed. The culture container 50 is provided on a member that is formed with the opening 51a, and in this configuration, a phase difference image of a cell in the culture container 50 passes through the opening 51a.

In the present embodiment, as the culture container 50, a well plate provided with a plurality of well plates in which cells are contained (in which one well corresponds to the container of the present disclosure) is used. In addition, as cells contained in the culture container 50, multipotential stem cells such as induced pluripotent stem (iPS) cells and embryonic stem (ES) cells, cells of nerves, the skin, the myocardium and the liver, which are differentiated and induced from a stem cell, cells of the skin, the retina, the myocardium, blood corpuscles, nerves, and organs extracted from a human body, and the like, may be used.

Figure 8:
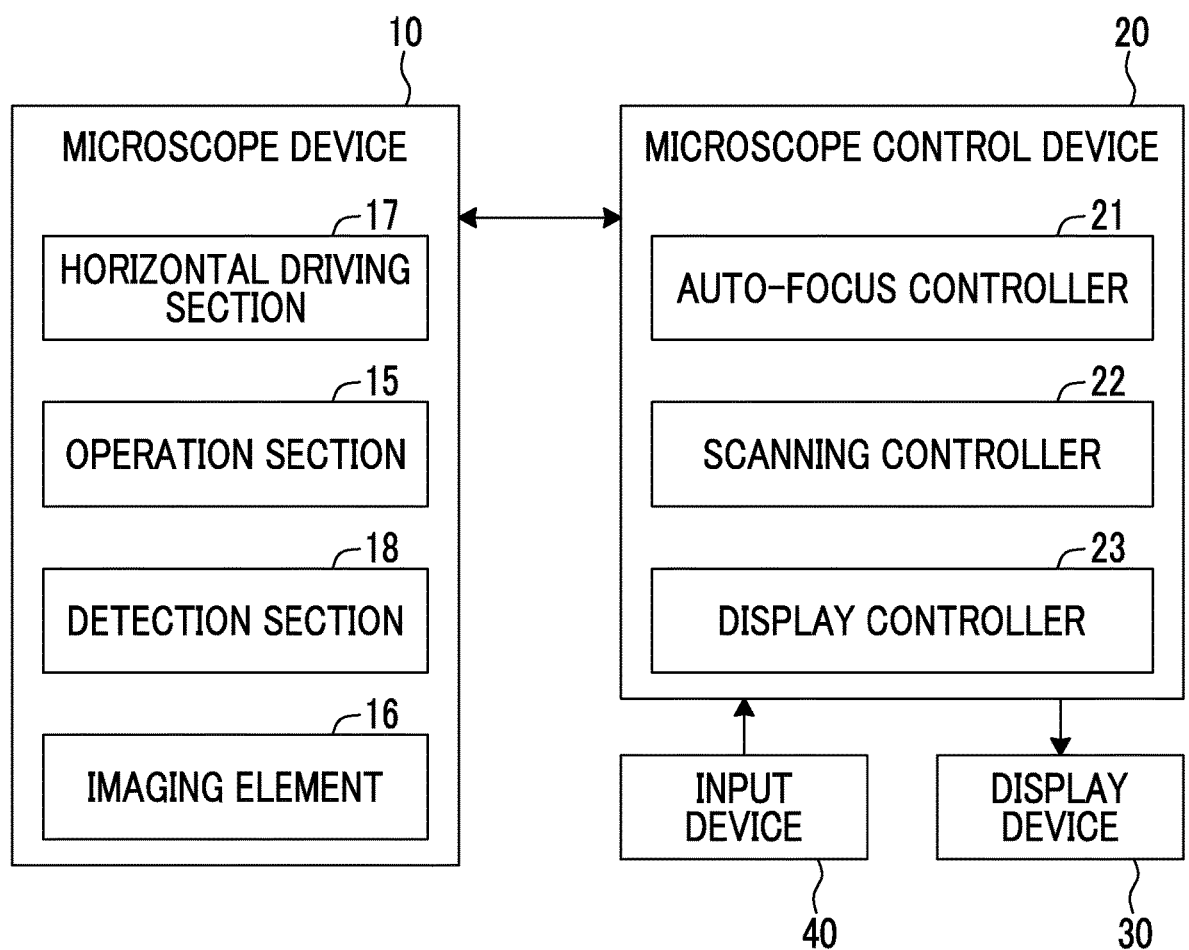
FIG. 8 is a block diagram showing a schematic configuration of the microscope observation system that uses the observation device according to the embodiment of the present disclosure.

The stage 51 is configured to be moved in an X direction and a Y direction that are orthogonal to each other by a horizontal driving section 17 (see FIG. 8). The X direction and the Y direction are directions that are orthogonal to a Z direction, and are directions that are orthogonal to each other in a horizontal plane.

The slit plate 13 has a configuration in which a ring-shaped slit through which white light passes is formed in a light-shielding plate that shields white light emitted from the white light source 11, and ring-shaped illumination light L is formed as the white light passes through the slit.

Figure 3:
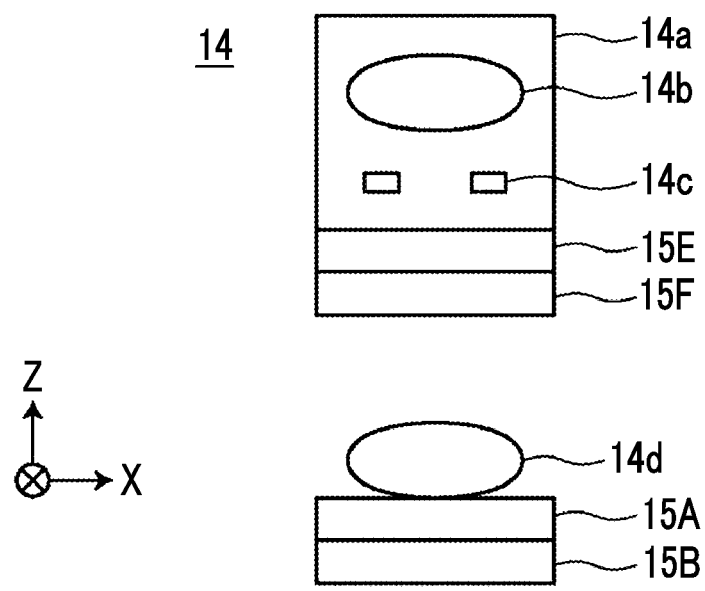
FIG. 3 is a schematic diagram showing a configuration of an imaging optical system.

FIG. 3 is a diagram showing a detailed configuration of the imaging optical system 14. The imaging optical system 14 includes a phase difference lens 14a and an imaging lens 14d, as shown in FIG. 3. The phase difference lens 14a includes an objective lens 14b and a phase plate 14c. The phase plate 14c has a configuration in which a phase ring is formed in a transparent plate that is transparent with respect to a wavelength of the illumination light L. The size of the slit of the above-described slit plate 13 is in a cooperative relation with the phase ring of the phase plate 14c.

The phase ring has a configuration in which a phase membrane that shifts a phase of incident light by ¼ of a wavelength and a dimmer filter that dims incident light are formed in a ring shape. The phase of direct light incident onto the phase ring shifts by ¼ of a wavelength after passing through the phase ring, and its brightness is weakened. On the other hand, most of diffracted light diffracted by an observation target passes through the transparent plate of the phase plate 14c, and its phase and brightness are not changed.

The phase difference lens 14a having the objective lens 14b is moved in the optical axis direction of the objective lens 14b by the fifth operation section 15E of the operation section 15 shown in FIG. 1. The fifth operation section 15E includes an actuator such as a piezoelectric element, for example. In this embodiment, the optical axis direction of the objective lens 14b and a Z direction (vertical direction) are the same direction. As the objective lens 14b is moved in the Z direction, an auto-focus control is performed, and contrast of a phase difference image captured by the imaging element 16 is adjusted.

Further, a configuration in which a magnification of the phase difference lens 14a is changeable may be used. Specifically, a configuration in which the phase difference lenses 14a or the imaging optical systems 14 having different magnifications are interchangeable may be used. The interchange between the phase difference lens 14a and the imaging optical systems 14 may be automatically performed, or may be manually performed by a user.

Further, the objective lens 14b is formed of a liquid lens whose focal length can be changed. As long as the focal length can be changed, the objective lens 14b is not limited to the liquid lens, and any other lens such as a liquid crystal lens or a shape deformable lens may be used. In the objective lens 14b, an applied voltage is changed by the sixth operation section 15F in the operation section 15 shown in FIG. 1, and thus, the focal length is changed. Thus, the focal length of the imaging optical system 14 is changed. Due to the change of the focal length of the objective lens 14b, similarly, the auto-focus control is performed, and the contrast of the phase difference image captured by the imaging element 16 is adjusted.

The imaging lens 14d receives a phase difference image passed through the phase difference lens 14a, so that an image is formed on the imaging element 16 from the phase difference image. In the present embodiment, the imaging lens 14d is formed of a liquid lens whose focal length can be changed. As long as the focal length can be changed, the objective lens 14b is not limited to the liquid lens, and any other lens such as a liquid crystal lens or a shape deformable lens may be used. In the imaging lens 14d, an applied voltage is changed by the first operation section 15A in the operation section 15 shown in FIG. 1, and the focal length is changed. Thus, the focal length of the imaging optical system 14 is changed. Due to the change of the focal length of the imaging lens 14d, similarly, the auto-focus control is performed, and the contrast of the phase difference image captured by the imaging element 16 is adjusted.

The imaging lens 14d is moved in the optical axis direction of the imaging lens 14d by the second operation section 15B in the operation section 15 shown in FIG. 1. The second operation section 15B includes an actuator such as a piezoelectric element, for example. In this embodiment, the optical axis direction of the imaging lens 14d and the Z direction (vertical direction) are the same direction. As the imaging lens 14d is moved in the Z direction, the auto-focus control is performed, and the contrast of the phase difference image captured by the imaging element 16 is adjusted.

The imaging element 16 captures an image on the basis of the phase difference image formed by the imaging lens 14d. As the imaging element 16, a charge-coupled device (CCD) image sensor, a complementary metal-oxide semiconductor (CMOS) image sensor, or the like may be used. As the imaging element, an imaging element in which color filters of red, green, and blue (R, and B) are provided may be used, or a monochromic imaging element may be used.

Further, the imaging element 16 is moved in the Z direction by the third operation section 15C in the operation section 15 shown in FIG. 1. The third operation section 15C includes an actuator such as a piezoelectric element, for example. In the present embodiment, a direction perpendicular to an imaging surface of the imaging element 16 and the Z direction are the same direction. As the imaging element 16 is moved in the Z direction, similarly, the auto-focus control is performed, and the contrast of the phase difference image captured by the imaging element 16 is adjusted.

Further, the stage 51 is moved in the Z direction by the fourth operation section 15D, and thus, the culture container 50 is moved in the Z direction. The fourth operation section 15D includes an actuator such as a piezoelectric element, for example. In the present embodiment, a direction perpendicular to a surface of the stage 51 on which the culture container 50 is provided and the Z direction are the same direction. As the stage 51 is moved in the Z direction, similarly, the auto-focus control is performed, and the contrast of the phase difference image captured by the imaging element 16 is adjusted.

Figure 4:
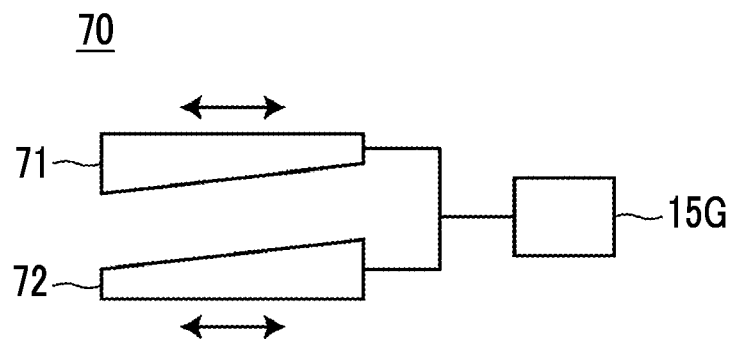
FIG. 4 is a schematic diagram showing a configuration of a focal length changing optical system.

FIG. 4 is a schematic diagram showing a configuration of the focal length changing optical system. As shown in FIG. 4, the focal length changing optical system 70 includes a circular first wedge prism 71 and a circular second wedge prism 72. The seventh operation section 15G moves the first wedge prism 71 and the second wedge prism 72 to be synchronized with each other in opposite directions. With this configuration, focal positions of the imaging optical system 14 are changed. The change of the focal position means that the focal length increases or decreases. Thus, as the focal position of the imaging optical system 14 is changed, the focal length of the imaging optical system 14 is changed. In the present embodiment, the change of the focal length of the imaging optical system 14 includes the change of the focal length of the imaging lens 14d by the first operation section 15A, and the change of the objective lens 14b by the sixth operation section 15F, and additionally, the change of the focal position of the imaging optical system 14 due to the change of the focal length of the imaging optical system 14 by the seventh operation section 15G.

The first and second wedge prisms 71 and 72 are prisms in which two surfaces that can be a light incident surface and a light emitting surface are not parallel, that is, one surface is inclined with respect to the other surface. In the following description, a surface arranged perpendicular to the optical axis is referred to as a right-angled surface, and a surface arranged inclined with respect to the optical axis is referred to as a wedge surface. The wedge prisms 71 and 72 are prisms that deflect light that is incident perpendicularly to the right-angle surfaces. The seventh operation section 15G includes an actuator such as a piezoelectric element, for example, and moves the first wedge prism 71 and the second wedge prism 72 to be synchronized with each other in opposite directions on the basis of control signals output from an auto-focus controller 21 (which will be described later), while maintaining the right-angled surfaces in parallel. That is, in a case where the first wedge prism 71 is moved rightward in FIG. 4, the second wedge prism 72 is moved leftward. Conversely, in a case where the first wedge prism 71 is moved leftward in FIG. 4, the second wedge prism 72 is moved rightward. As described above, by moving the first and second wedge prisms 71 and 72, an optical path length of light emitted from the imaging optical system 14 is changed, so that the focal position of the imaging optical system 14 is changed, to thereby make it possible to change the focal length. Accordingly, the auto-focus control is performed, and contrast of a phase difference image captured by the imaging element 16 is adjusted.

The detection section 18 detects a Z-directional (vertical direction) position of the culture container 50 installed on the stage 51. Specifically, the detection section 18 includes a first auto-focus displacement sensor 18a and a second auto-focus displacement sensor 18b. The first and second auto-focus displacement sensors 18a and 18b correspond to displacement sensors of the present disclosure.

The first auto-focus displacement sensor 18a and the second auto-focus displacement sensor 18b are provided in parallel in the X direction as shown in FIG. 1 with the imaging optical system 14 being interposed therebetween. The first auto-focus displacement sensor 18a and the second auto-focus displacement sensor 18b in this embodiment are laser displacement meters, which irradiate the culture container 50 with laser light and detect its reflection light to detect a Z-directional position of a bottom surface of the culture container 50. The bottom surface of the culture container 50 refers to a boundary surface between a bottom portion of the culture container 50 and cells that are observation targets, that is, a surface on which the observation targets are placed.

Information on the Z-directional position of the culture container 50 detected by the detection section 18 is output to the auto-focus controller 21, and the auto-focus controller 21 controls the operation section 15 on the basis of the input position information to perform the auto-focus control.

More specifically, in the microscope device 10 according to the embodiment, before the imaging optical system 14 reaches a predetermined observation position in the culture container 50 on the stage 51, information on the Z-directional position of the culture container 50 at the observation position is precedently detected by the first or second auto-focus displacement sensor 18a or 18b, and in a case where the imaging optical system 14 reaches the observation position, the operation section 15 is controlled on the basis of the position information detected by the first or second auto-focus displacement sensor 18a or 18b to perform the auto-focus control.

Here, in a case where a well plate having a plurality of wells is used as the culture container 50 as in the present embodiment, if the auto-focus control is performed from a time point when the imaging optical system 14 reaches each observation position for all observation positions in the well plate as in the related art, in performing the auto-focus control at an observation position immediately after a boundary portion between adjacent wells in the scanning direction of the observation position, that is, an initial observation position of a well on a front side in the scanning direction among adjacent wells is performed, it takes a long time to perform the auto-focus control due to a difference in thicknesses of bottom portions of the respective wells. The scanning direction of the observation position described above is a direction opposite to the movement direction of the stage 51.

Figure 5:
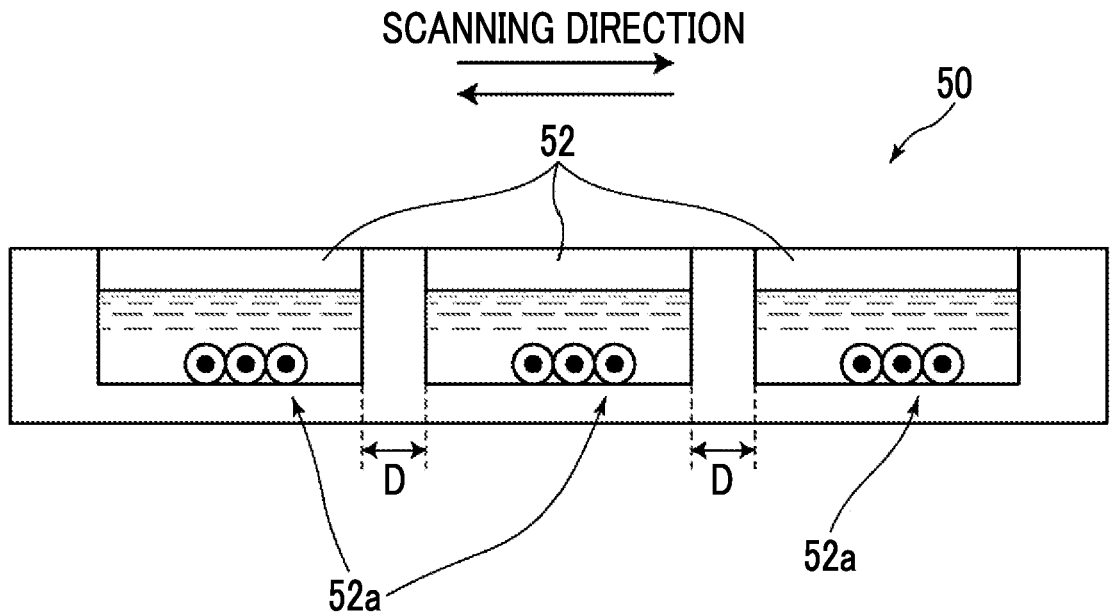
FIG. 5 is a diagram illustrating a boundary portion of each well of a well plate.

FIG. 5 is a schematic cross-sectional view of an example of the culture container 50 (well plate) provided with a plurality of wells 52. "D" shown in FIG. 5 is a boundary portion between adjacent wells, and "52a" is a bottom portion of the well 52. In addition, as shown in FIG. 4, the thickness of the bottom portion 52a of each well 52 varies depending on manufacturing variations.

Further, in a case where the scanning is performed in a two-dimensional manner while reciprocating the stage 51 in the X direction and moving the stage 51 in the Y direction, since the imaging optical system 14 passes the boundary of the well 52 many times, the time loss of the auto-focus control when straddling the boundary portion D of the well 52 becomes large.

Figure 6:
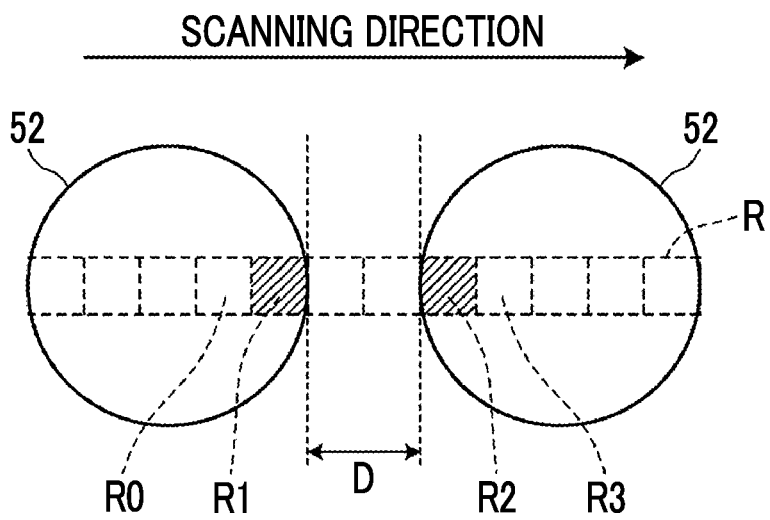
FIG. 6 is a diagram illustrating an auto-focus control in the microscope observation system that uses the observation device according to the embodiment of the present disclosure.

Accordingly, in the present embodiment, as shown in FIG. 6, a timing when the auto-focus control is started is switched between an observation position R2 immediately after the boundary portion D between the adjacent wells 52 and an observation position other than the observation position R2 immediately after the boundary portion D. Specifically, in the present embodiment, the auto-focus control of the observation position R2 immediately after the boundary portion D is started from a time point when the auto-focus control of the observation positionR1 immediately before the boundary portion is terminated. A rectangular range indicated by a broken line in FIG. 6 indicates each observation position R.

That is, in the present embodiment, since it is not necessary to perform imaging by the auto-focus control for an observation position included in the boundary portion D between the adjacent wells 52, the auto-focus control is not performed for the observation position included in the boundary portion D, and the auto-focus control for the observation position R2 immediately after the boundary portion D is performed using a scanning time for the observation position included in the boundary portion D. FIG. 6 is a diagram showing an example of a start timing and an end timing of the auto-focus control of each of the observation positions R0 to R3 near the boundary portion D of the well 52. f0 to f3 shown in FIG. 7 are times during which the auto-focus control is performed for the respective observation positions R0 to R3, Tx is a scanning time between adjacent observation positions (a time during which the imaging optical system 14 is relatively moved with respect to the stage 51), and Td is a scanning time from the observation position R2 to the observation position R3.

Figure 7:
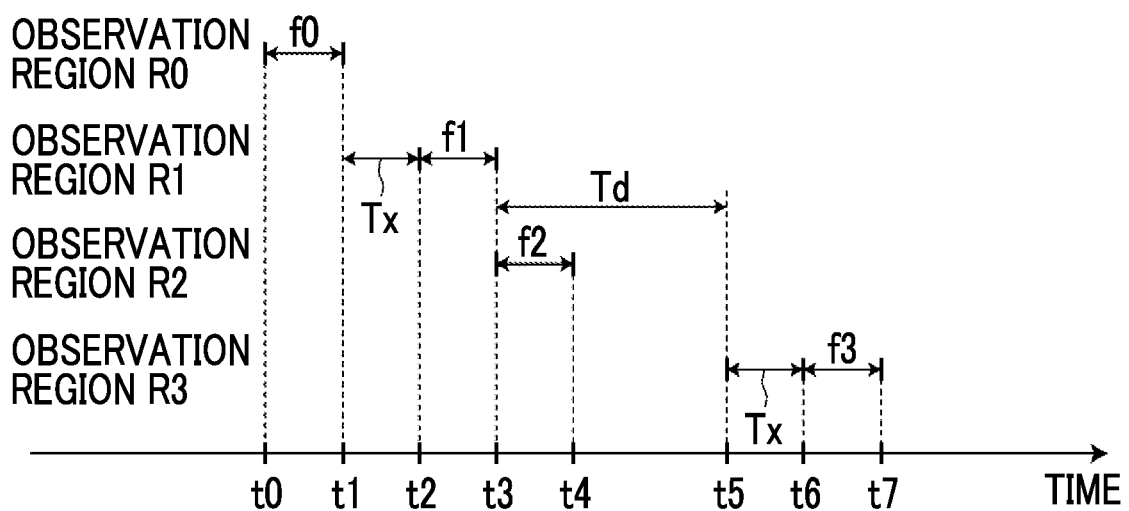
FIG. 7 is a diagram illustrating an example of a start timing of the auto-focus control according to the present disclosure.

As shown in FIG. 7, for the observation position R0, the auto-focus control starts at a time t0, and the auto-focus control ends at a time t1. Then, after scanning from the observation position R0 to the observation position R1, the auto-focus control of the observation position R1 is started at a time t2, and the auto-focus control ends at a time t3. Then, the auto-focus control of the observation position R2 is started from the time t3 when the auto-focus control of the observation position R1 ends, and at a time t4 before a time t5 when the imaging optical system 14 reaches the observation position R2, the auto-focus control of the observation position R2 ends. That is, during a scanning time Td from the observation position R1 to the observation position R2, the auto-focus control of the observation position R2 ends.

Then, at the time t5 when the imaging optical system 14 reaches the observation position R2, since the auto-focus control of the observation position R2 has already ended, a phase difference image at the observation position R2 is immediately captured, and the scanning is performed toward the next observation position R3. Then, after scanning from the observation position R2 to the observation position R3, the auto-focus control of the observation position R3 starts at a time t6, and the auto-focus control ends at a time t7.

In the case of the auto-focus control in the related art, since the auto-focus control of the observation position R2 is started from a time point when the imaging optical system 14 reaches the observation position R2 (the time t5 in FIG. 7), its imaging time becomes longer, and particularly, in a case where the thickness of the bottom portion of the well 52 varies, the time loss becomes larger.

In the present embodiment, as described above, it is possible to reduce the imaging time by making the start timing of the auto-focus control of the observation position R2 immediately after the boundary portion D earlier.

As for the observation positions other than the observation position R2 immediately after the boundary portion D, as described above, the auto-focus control is started from the time point when each observation position is reached. Further, in the present embodiment, the auto-focus control of the observation position R2 immediately after the boundary portion D is started from the time point t3 when the auto-focus control of the observation position R1 immediately before the boundary portion D ends, but the present disclosure is not limited to thereto, and the auto-focus control of the observation position R2 immediately after the boundary portion D may be started at any other time point as long as it is before the time t5 when the imaging optical system 14 reaches the observation position R2 after the time point t3 when the auto-focus control of the observation position R ends. That is, any other time point during Td shown in FIG. 7 may be used.

Further, in the present embodiment, the time for the auto-focus control of the observation position R2 immediately after the boundary portion D (for example, the time Td shown in FIG. 7, which is the time from the time point when the imaging optical system 14 reaches the observation position R1 to the time point when the imaging optical system 14 reaches the observation position R2) is set to be longer than the time for the auto-focus control of the observation position other than the observation position R2 immediately after the boundary portion D (for example, the time from the time t0 to the time t2 shown in FIG. 7, which is the time from the time point when the imaging optical system 14 reaches the observation position R0 to the time point when the imaging optical system 14 reaches the observation position R1).

In addition, in a case where the auto-focus control of the observation position R2 immediately after the boundary portion D is performed as described above, it is necessary to specify coordinates of the observation position R1 immediately before the boundary portion D and the observation position R2 immediately after the boundary portion D in the X-Y plane. That is, it is necessary to specify the boundary portion D. Therefore, in the present embodiment, the boundary portion D between the adjacent wells 52 is detected by the above-described first or second auto-focus displacement sensors 18a or 18b. Specifically, since the bottom surface of the well 52 does not exist at the boundary portion D, a detection signal detected by the first or second auto-focus displacement sensor 18a or 18b obviously varies. Accordingly, for example, it is possible to detect the boundary portion D by determining whether the detection signal detected by the first or second auto-focus displacement sensors 18a or 18b is within a range of a preset threshold value.

Then, a configuration of the microscope control device 20 that controls the microscope device 10 will be described. FIG. 8 is a block diagram showing a configuration of the microscope observation system according to this embodiment. With respect to the microscope device 10, a block diagram of a partial configuration controlled by respective sections of the microscope control device 20 is shown.

The microscope control device 20 generally controls the microscope device 10, and particularly, includes the auto-focus controller 21, the scanning controller 22, and the display controller 23.

The microscope control device 20 is configured of a computer including a central processing unit, a semiconductor memory, a hard disk, and the like, and an embodiment of an observation device control program of the present disclosure is installed in the hard disk. Further, as the observation device control program is executed by the central processing unit, the auto-focus controller 21, the scanning controller 22, and the display controller 23 shown in FIG. 8 execute their functions.

The auto-focus controller 21 performs the auto-focus control by operating the operation section 15 on the basis of the information on the Z-directional position of the culture container 50 detected by the detection section 18 as described above. Further, as described above, the auto-focus controller 21 of the present embodiment switches a starting timing of the auto-focus control between the observation position immediately after the boundary portion between the adjacent wells and the observation position other than the observation position immediately after the boundary portion.

Here, the auto-focus controller 21 stores relationships between the information on the Z-directional position of the culture container 50, a voltage applied to the imaging lens 14d for changing the focal length of the imaging lens 14d, the amount of movement of the imaging lens 14d in the optical axis direction, the amount of movement of the imaging element 16 in the optical axis direction, the amount of movement of the stage 51 in the optical axis direction, the amount of movement of the objective lens 14b in the optical axis direction, a voltage applied to the objective lens 14b for changing the focal length of the objective lens 14b, and the amount of movement of the focal length changing optical system 70 in advance as a table. This table is referred to as a first table.

The auto-focus controller 21 respectively obtains the voltage applied to the imaging lens 14d for changing the focal length of the imaging lens 14d, the amount of movement of the imaging lens 14d in the optical axis direction, the amount of movement of the imaging element 16 in the optical axis direction, the amount of movement of the stage 51 in the optical axis direction, the amount of movement of the objective lens 14b in the optical axis direction, the voltage applied to the objective lens 14b for changing the focal length, and the amount of movement of the focal length changing optical system 70, with reference to the first table, on the basis of the input information on the Z-directional position of the culture container 50. In the following description, the voltage applied to the imaging lens 14d for changing the focal length of the imaging lens 14d, the amount of movement of the imaging lens 14d in the optical axis direction, the amount of movement of the imaging element 16 in the optical axis direction, the amount of movement of the stage 51 in the optical axis direction, the amount of movement of the objective lens 14b in the optical axis direction, the voltage applied to the objective lens 14b for changing the focal length of the objective lens 14b, and the amount of movement of the focal length changing optical system 70 are referred to as focus control amounts.

The auto-focus controller 21 outputs control signals corresponding to the focus control amounts to the first operation section 15A to the seventh operation section 15G in order to control the operation section 15. Specifically, the focus control amount is acquired with reference to the first table on the basis of the position information of the stage 51 acquired as described later. Thus, the focal length of the imaging lens 14d is changed by the first operation section 15A, and thus, the focal length of the imaging optical system 14 is changed. Further, the imaging lens 14d is moved in the optical axis direction by the second operation section 15B. The imaging element 16 is moved in the optical axis direction by the third operation section 15C. Further, the stage 51 is moved in the optical axis direction by the fourth operation section 15D. In addition, the objective lens 14b is moved in the optical axis direction by the fifth operation section 15E. The focal length of the objective lens 14b is changed by the sixth operation section 15F, and thus, the focal length of the imaging optical system 14 is changed. Further, the focal position of the imaging optical system 14 is changed by the seventh operation section 15G and thus, the focal length of the imaging optical system 14 is changed. Through these seven operations, the auto-focus control is performed.

The change of the focal length of the imaging lens 14d by the first operation section 15A, the change of the focal length of the objective lens 14b by the sixth operation section 15F, and the change of the focal length changing optical system 70 by the seventh operation section 15G correspond to a first operation. The movement of the imaging lens 14d in the optical axis direction by the second operation section 15B corresponds to a second operation. The movement of the imaging element 16 in the optical axis direction by the third operation section 15C corresponds to a third operation. The movement of the stage 51 in the optical axis direction by the fourth operation section 15D corresponds to a fourth operation. The movement of the objective lens 14b in the optical axis direction by the fifth operation section 15E corresponds to a fifth operation.

The scanning controller 22 drives and controls the horizontal driving section 17, to thereby move the stage 51 in the X direction and the Y direction, and move the culture container 50 in the X direction and the Y direction. The horizontal driving section 17 is configured by an actuator such as a piezoelectric element.

Figure 9:
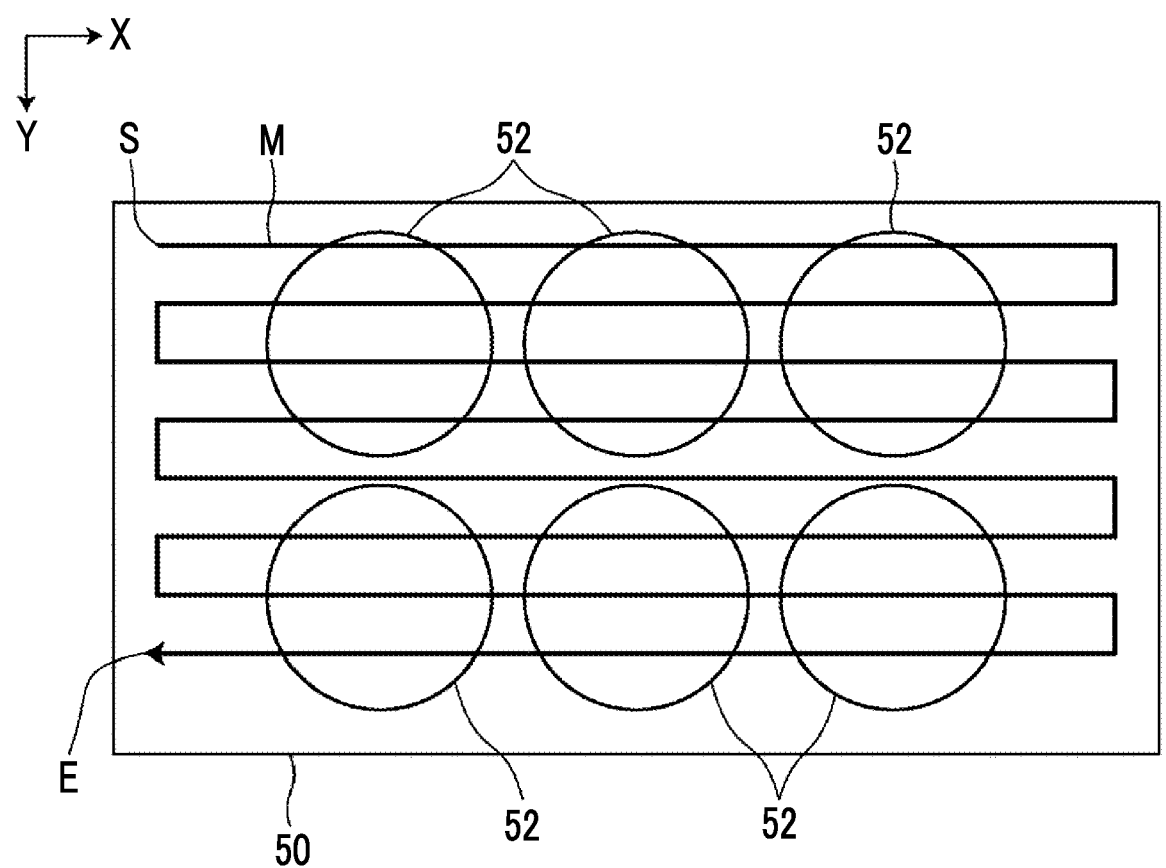
FIG. 9 is a diagram showing a scanning position of an observation position in a culture container.

In this embodiment, as described above, the stage 51 is moved in the X direction and the Y direction under the control of the scanning controller 22, the observation position in the culture container 50 is scanned in a two-dimensional manner, and a phase difference image at each observation position is captured. FIG. 9 is a diagram showing a scanning position of an observation position in the culture container 50 using a solid line M. In this embodiment, a well plate having six wells 52 is used as the culture container 50.

As shown in FIG. 9, the observation region in the culture container 50 is scanned from a scanning start point S to a scanning end point E along the solid line M, by the movement of the stage 51 in the X direction and the Y direction. That is, the observation region is scanned in a positive direction (a rightward direction in FIG. 9) of the X direction, is scanned in the Y direction (a downward direction in FIG. 9), and then, is scanned in a reverse negative direction (in a leftward direction in FIG. 9). Then, the observation region is scanned in the Y direction again, and then, is scanned in the positive direction of the X direction again. In this way, by repeating the reciprocating movement of the stage 51 in the X direction and the movement of the stage 51 in the Y direction, the observation region is scanned in the culture container 50 in a two-dimensional manner.

Next, returning to FIG. 8, the display controller 23 combines phase difference images at the respective observation positions imaged by the microscope device 10 to generate one composite phase difference image, and displays the composite phase difference image on the display device 30.

The display device 30 displays the composite phase difference image generated by the display controller 23 as described above. For example, the display device 30 includes a liquid crystal display, or the like. Further, the display device 30 may be formed by a touch panel, and may also be used as the input device 40.

The input device 40 includes a mouse, a keyboard, and the like, and receives various setting inputs by the user. The input device 40 according to this embodiment receives a setting input such as a change command of the magnification of the phase difference lens 14a or a change command of the moving velocity of the stage 51, for example.

Figure 10:
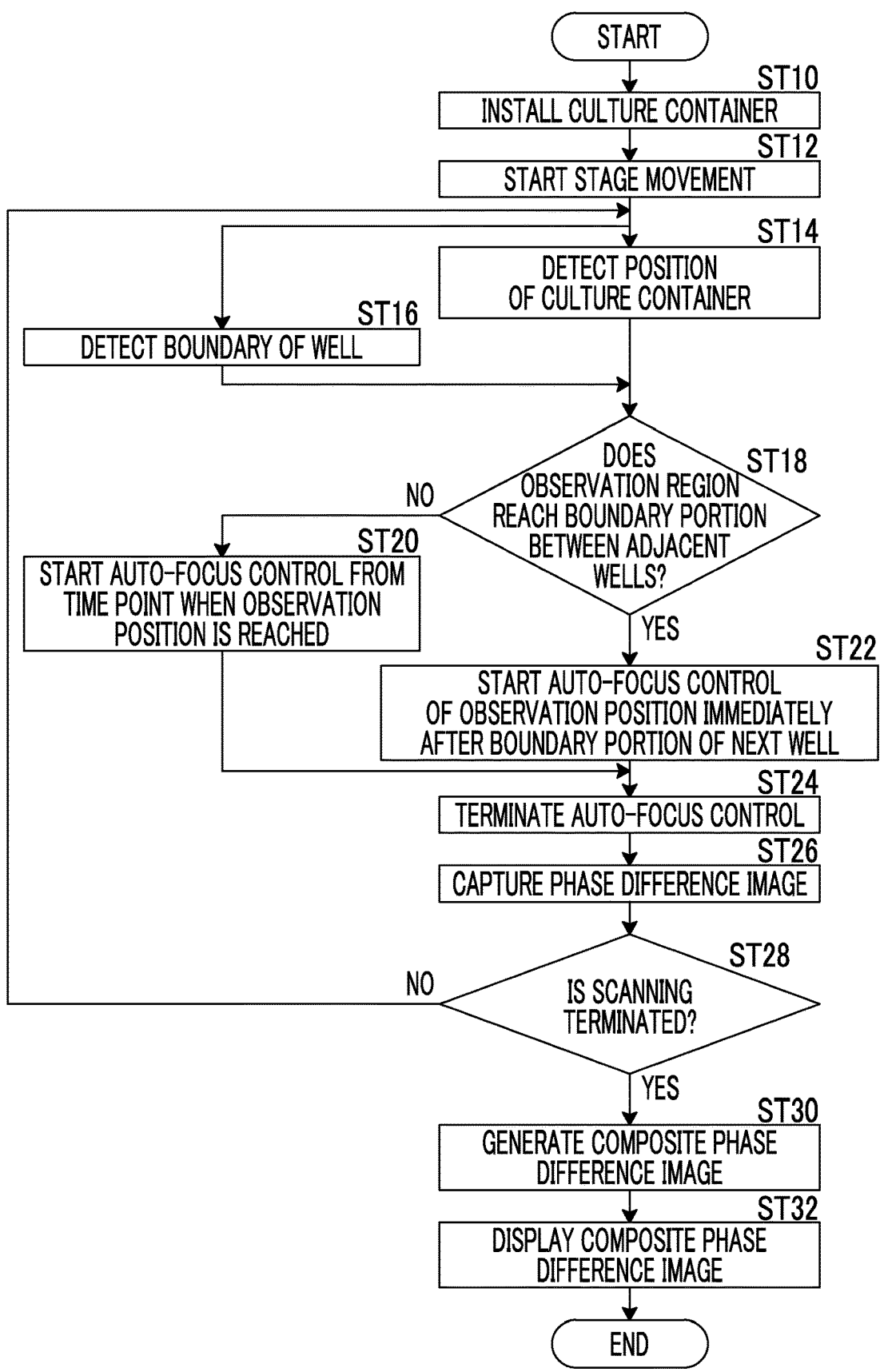
FIG. 10 is a flowchart illustrating an operation of the microscope observation system that uses the observation device according to the embodiment of the present disclosure.

Next, an operation of the microscope observation system according to this embodiment will be described with reference to a flowchart shown in FIG. 10. First, the culture container 50 in which cells that are observation targets are contained is provided on the stage 51 (step ST10). Then, the stage 51 is moved so that the observation position of the imaging optical system 14 is set to the position of the scanning start point S shown in FIG. 9, and the movement of the stage 51 is started (step ST12).

Here, in this embodiment, as described above, the Z-directional position of the culture container 50 is precedently detected with respect to each observation position, and at a time point when the imaging optical system 14 is moved up to the observation position, imaging for a phase difference image is performed. Further, the detection of the Z-directional position of the culture container 50 and the capturing of the phase difference image are performed while scanning the observation position, and capturing of a phase difference image at a certain observation position and detection of the Z-directional position of the culture container 50 at a forward position in the scanning direction with reference to the observation position are performed in parallel.

Figure 11:
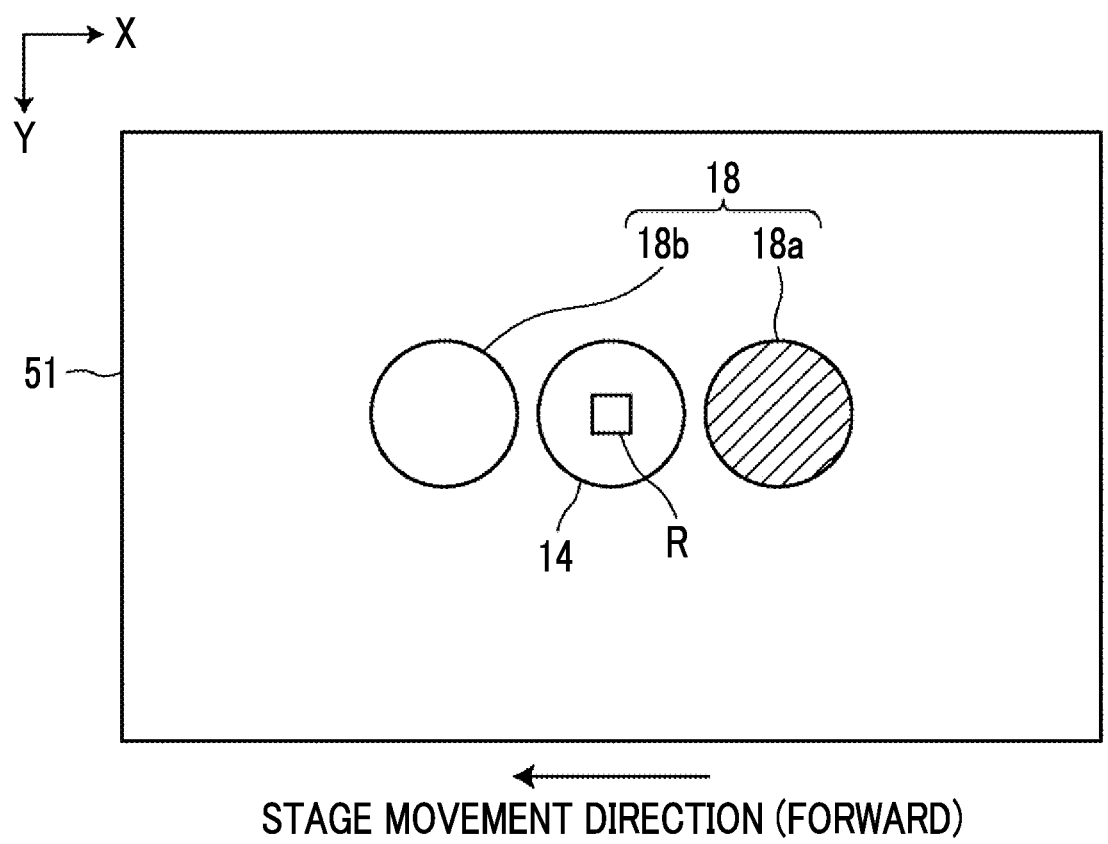
FIG. 11 is a schematic diagram illustrating an operation of the microscope observation system in a case where the stage is moving forward.

Specifically, in a case where the stage 51 is moved forward in an arrow direction shown in FIG. 11, the Z-directional position of the culture container 50 is detected by the first auto-focus displacement sensor 18a (step ST14), and information on the detected position is acquired by the auto-focus controller 21. The auto-focus controller 21 stores the acquired information on the Z-directional position of the culture container 50 together with X-Y coordinates of the observation position of the culture container 50.

Further, the first auto-focus displacement sensor 18a performs a process of detecting a boundary portion of a well together with the detection of the Z-directional position of the culture container 50 (step ST16). In a case where the boundary portion of the well is detected, X-Y coordinates thereof are stored.

Then, in step ST14, the imaging optical system 14 moves toward the observation position where the position of the culture container 50 is detected by the first auto-focus displacement sensor 18a and the auto-focus control of the observation position is performed, but as described above, the start timing of the auto-focus control is switched depending on the observation position.

Specifically, in a case where the observation position has not reached the boundary portion between the adjacent wells (step ST18; NO), the auto-focus control is started from a time point when each observation position has been reached (step ST20). Specifically, the focus control amount is acquired on the basis of the information on the Z-directional position of the culture container 50 at each observation position, and the auto-focus control is performed on the basis of the focus control amount.

On the other hand, in a case where the observation position immediately before the boundary portion between the adjacent wells has been reached, the auto-focus control of an observation position immediately after a boundary portion of the next well (the first observation position of the next well) starts from a time point when the auto-focus control of the observation position immediately before the boundary portion ends (step ST22). That is, the focus control amount is acquired on the basis of the information on the Z-directional position of the culture container 50 at the observation position immediately after the boundary portion, and the auto-focus control is performed on the basis of the focus control amount.

Then, after the auto-focus control ends for each observation position (step ST24), imaging for a phase difference image is performed (step ST26). The phase difference image at each observation position is output from the imaging element 16 to the display controller 23 for storage.

Figure 12:
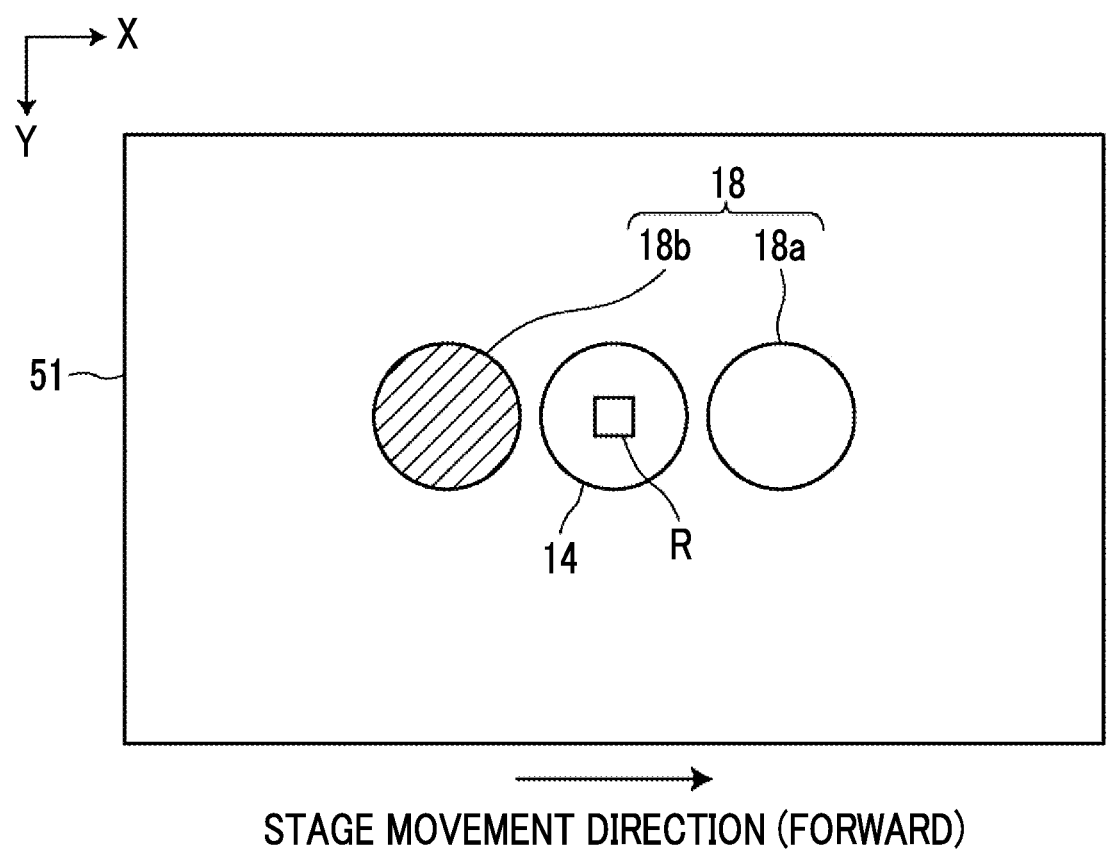
FIG. 12 is a schematic diagram illustrating another operation of the microscope observation system in a case where the stage is moving forward.

Further, in a case where the forward movement is terminated, and then, the movement is switched to a returning movement as shown in FIG. 12, a displacement sensor to be used is switched from the first auto-focus displacement sensor 18*a* to the second auto-focus displacement sensor 18*b*.

In addition, in a case where the entire scanning is not terminated at this time point (step ST28; NO), the stage 51 is reversely moved again, and then, the processes of steps ST14 to ST28 are performed.

The displacement sensor to be used is switched whenever the movement direction of the stage 51 is switched, and the processes of steps ST14 to ST26 are repeatedly performed until the entire scanning is terminated. Further, at a time point when the observation position reaches the position of the scanning end point E shown in FIG. 9, the entire scanning is terminated (step ST28; YES).

After the entire scanning is terminated, the display controller 23 combines phase difference images in the respective observation regions R to generate a composite phase difference image (step ST30), and displays the generated composite phase difference image on the display device 30 (step ST32).

According to the microscope observation system of the above-described embodiment, in a case where the auto-focus control for each observation position in the culture container 50 is performed, since the start timing of the auto-focus control for each observation position is switched on the basis of the boundary portion D between the adjacent wells 52 in the scanning direction of the observation position, it is possible to efficiently perform the auto-focus control, to thereby reduce the imaging time.

In addition, since the auto-focus control is performed by the first to seventh operation sections 15A to 15G, it is possible to perform the auto-focus control with high speed compared with a case where the auto-focus control is performed by only one operation.

Figure 13:
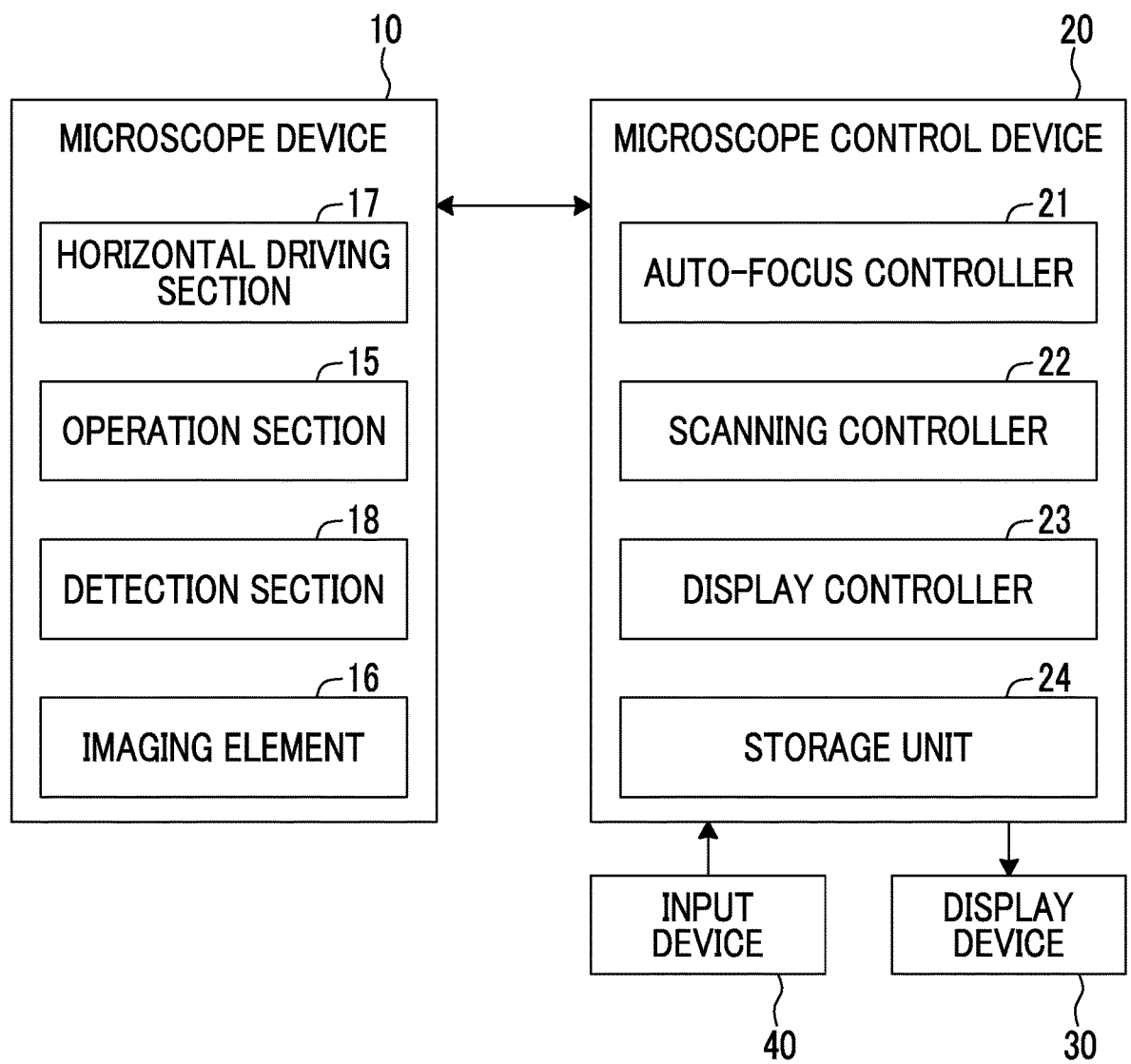
FIG. 13 is a block diagram showing a schematic configuration of the microscope observation system that uses the observation device according to the embodiment of the present disclosure.

In the above-described embodiment, a boundary portion between wells is detected by the first or second auto-focus displacement sensor 18*a* or 18*b*, but the present disclosure is not limited to thereto, and the boundary portion between the wells may be acquired and stored in advance. Specifically, as shown in FIG. 13, a storage unit 24 that stores information on the position of the boundary portion between the wells may be provided, and the auto-focus controller 21 may switch the start timing of the auto-focus control on the basis of the information on the position of the boundary portion stored in the storage unit 24.

In a case where the information on the position of the boundary portion between the wells is stored in this manner, identification information may be assigned to each culture container 50, and a table (hereinafter, referred to as a second table) in which the identification information is associated with the information on the position of the boundary portion between the wells may be set in advance. By providing such a second table, for example, even in a case where the culture container 50 having a different number of wells is installed, it is possible to appropriately switch the start timing of the auto-focus control as described above. The identification information of the culture container 50 may be set and input by a user using the input device 40, or a barcode or an RFID (radio frequency identification) tag storing the identification information may be provided for the culture container 50, and the identification information may be read therefrom.

In the microscope observation system of this embodiment, the boundary portion between the wells is detected by the first and second auto-focus displacement sensors 18*a* and 18*b*, but the present disclosure is not limited thereto, and a well boundary detecting sensor other than the first and second auto-focus displacement sensors 18*a* and 18*b* may be provided.

In the microscope observation system of the above embodiment, a well plate having a plurality of wells 52 is used as the culture container 50, but a petri dish may be used as the container of the present disclosure, and a plurality of petri dishes may be installed on the stage 51. In the above-described embodiment, the start timing of the auto-focus control for each observation position is switched on the basis of the boundary portion between the adjacent wells 52 in the scanning direction of the observation position, but in a case where the plurality of petri dishes are installed on the stage 51, the start timing of the auto-focus control for each observation position may be set to be switched on the basis of a boundary portion between adjacent petri dishes in the scanning direction of the observation position.

Specifically, the above-described well 52 may be replaced with a petri dish, and the auto-focus control of an observation position immediately after a boundary portion of the petri dish may be started, for example, from a time point when the auto-focus control of an observation position immediately before the boundary portion is terminated. Then, for an observation position other than the observation position immediately after the boundary portion, the auto-focus control may be started from a time point when the imaging optical system 14 reaches the observation position.

Figure 14:
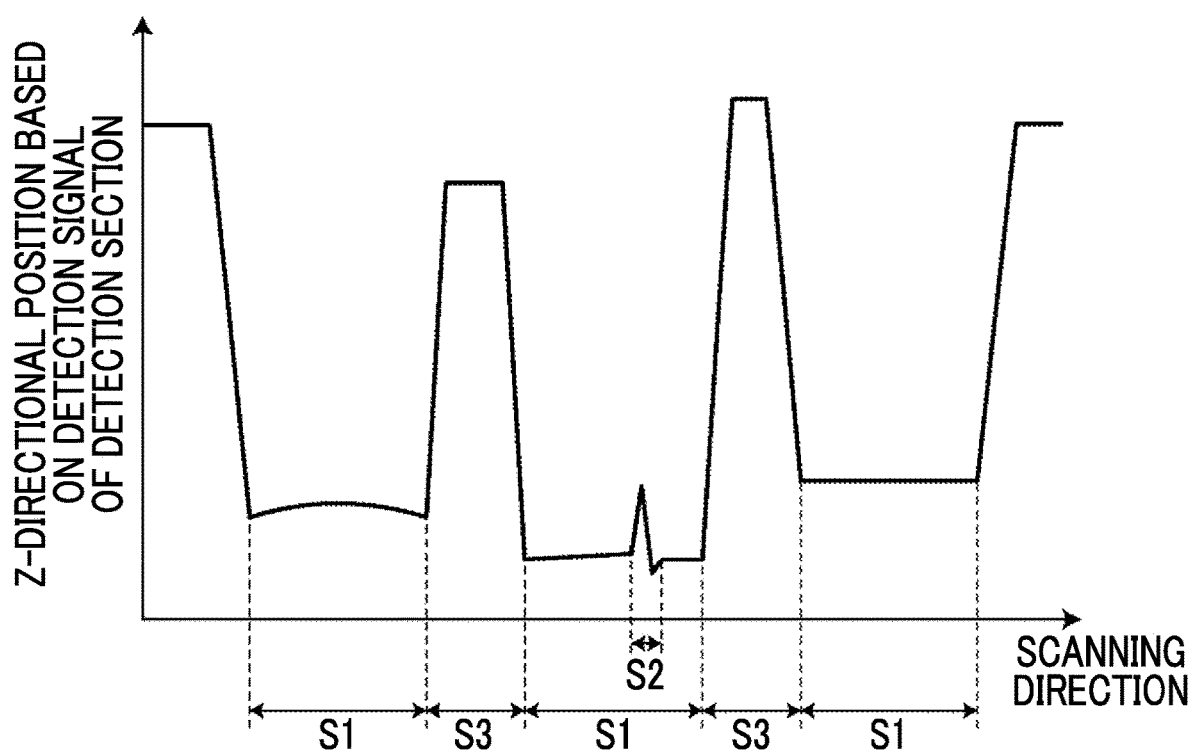

In the above embodiment, the Z-directional position of the bottom surface of the culture container 50 is detected, but for example, in a case where the bottom surface of the culture container 50 has a flaw or adhesion of dirt and a detection signal detected by the detection section 18 is abnormal, it is not possible to appropriately perform the auto-focus control. FIG. 14 is a diagram showing s Z-directional position based on a detection signal detected by the detection section 18 in a case where the bottom surface of the culture container 50 has a flaw or adhesion of dirt. A range of Si shown in FIG. 14 corresponds to a range of the bottom surface of each well 52, and a range of S3 corresponds to a range of the boundary portion D of the wells 52. Then, a range of S2 shown in FIG. 14 corresponds to a range of the flaw or adhesion of dirt on the bottom surface of the culture container 50.

Accordingly, in a case where the detection signal detected by the detection section 18 is abnormal, the auto-focus controller 21 may perform, for an observation position where the abnormal detection signal is detected, the auto-focus control based on a detection signal of the detection section 18 at an observation position immediately after the observation position in the scanning direction of the observation position. In the case of the detection signal as shown in FIG. 14, the detection signal detected by the detection section 18 is not used for the range of S2, and the auto-focus control is performed using detection signal of the observation position immediately before and/or immediately after the range of S2.

Specifically, for example, the auto-focus control of the observation position in the range of S2 may be performed using an average value of the detection signal of the observation position immediately before the range of S2 and the detection signal of the observation position immediately after the range of S2. Further, the detection signal of the observation position immediately before the range of S2 or the detection signal of the observation position immediately after the range of S2, instead of the average value may be used, and linear interpolation may be performed using a detection signal of an observation position immediately before the range of S2 and a detection signal of an observation position immediately after the range of S2 to acquire the detection signal of the observation position in the range of S2. Further, linear interpolation may be performed using detection signals of two or more observation positions before the range of S2 and detection signals of two or more observation positions after the range of S2, instead of the observation positions immediately before and immediately after the range of S2, to acquire the detection signal in the range of S2.

In the above-described embodiment, the observation position in the culture container 50 is scanned by moving the stage 51, but the present disclosure is not limited thereto, and an imaging system that includes the imaging optical system 14, the detection section 18, and the imaging element 16 may be configured to be moved. Further, both the stage 51 and the imaging system may be configured to be moved.

In the above-described embodiments, the operation section 15 performs the auto-focus control by the first to seventh operation sections 15A to 15G; but instead, only the first to fourth operation sections 15A to 15D, and the sixth to seventh operation sections 15F and 15G may be provided. Further, the auto-focus control may be performed using only one of the first to fourth operation sections 15A to 15D, and the sixth to seventh operation sections 15F and 15G. In this case, the auto-focus control may be further performed using the fifth operation section 15E. Further, only one of the first to fourth operation sections 15A to 15D, and the sixth to seventh operation sections 15F and 15G may be provided. In this case, similarly, the fifth operation section 15E may be further provided, and the auto-focus control may be configured to be performed using the fifth operation section 15E. In addition, the auto-focus control may be performed using a plurality of operation sections among the first to fourth operation sections 15A to 15D, and the sixth to seventh operation sections 15F and 15G. In this case, similarly, the auto-focus control may be performed further using the fifth operation section 15E.

Further, in the above-described embodiments, the focal length changing optical system 70 is disposed between the imaging optical system 14 and the imaging element 16, but may be disposed between the imaging optical system 14 and the stage 51.

In the above-described embodiments, the focal length of the imaging optical system 14 is changed by the first operation section 15A, the sixth operation section 15F, and the seventh operation section 15G, but the focal length of the imaging optical system 14 may be changed by only any one or two of the first operation section 15A, the sixth operation section 15F, and the seventh operation section 15G.

Further, in the above-described embodiments, the culture container 50 is moved in the optical axis direction by moving the stage 51 in the optical axis direction using the fourth operation section 15D. However, instead of moving the stage 51 in the optical axis direction, a mechanism for moving the culture container 50 in the optical axis direction may be provided, and only the culture container 50 may be moved in the optical axis direction.

Figure 15:
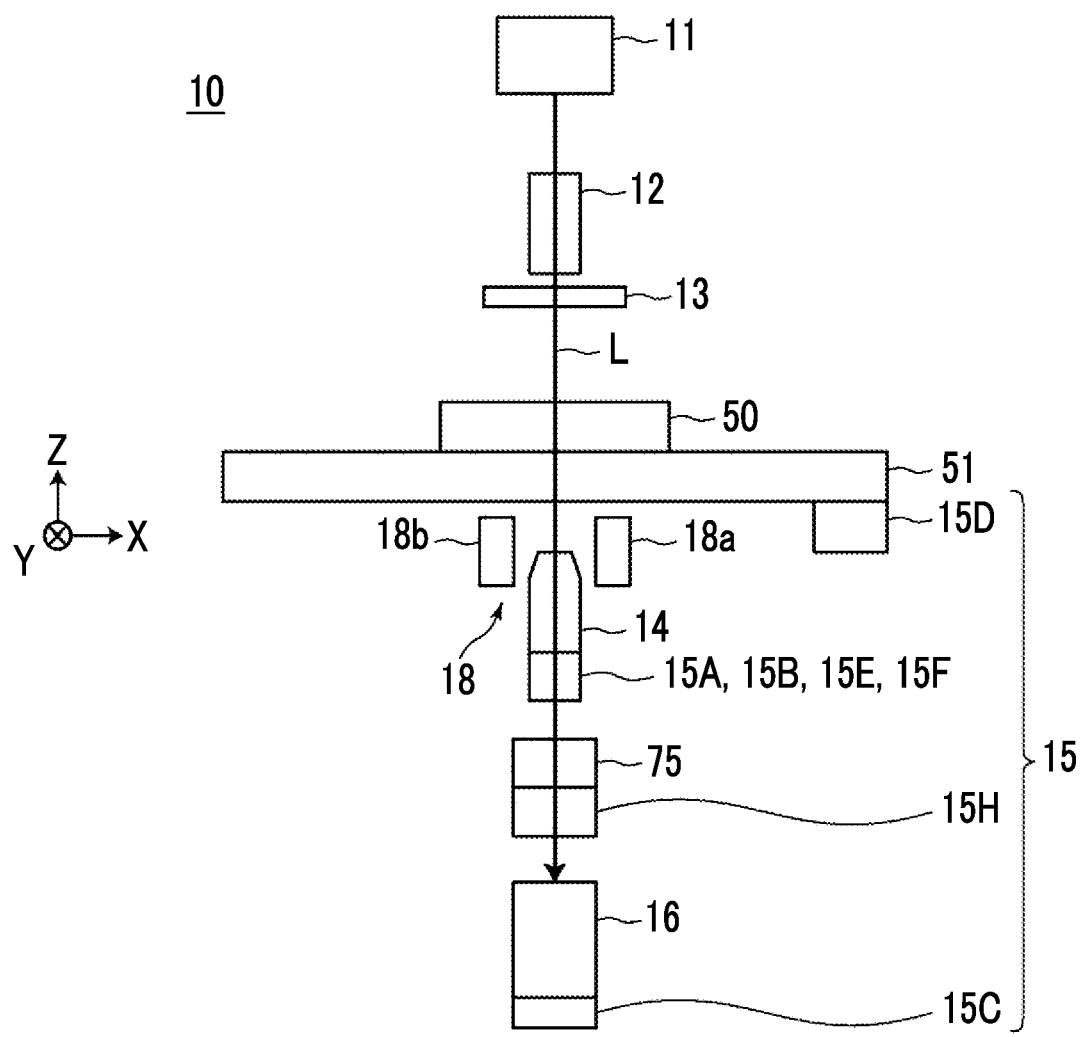
FIG. 15 is a diagram showing a schematic configuration of a modification example of the microscope observation system that uses the observation device according to the embodiment of the present disclosure.

Further, in the above-described embodiments, the optical system that moves the first and second wedge prisms 71 and 72 is used as the focal length changing optical system 70 for changing the focal length of the imaging optical system 14. However, an optical element capable of changing a focal length, such as a liquid lens, a liquid crystal lens, a shape deformable lens, or the like, may be used as the focal length changing optical system. For example, instead of the focal length changing optical system 70 for moving the first and second wedge prisms 71 and 72, as shown in FIG. 15, a focal length changing optical system 75 including an optical element capable of changing a focal length may be provided between the imaging optical system 14 and the imaging element 16. In this case, the focal length changing optical system 75 is configured such that an applied voltage is changed by an eighth operation section 15H to change the focal length. The focal length changing optical system 75 may be disposed between the imaging optical system 14 and the stage 51. The focal length changing optical system 75 may be disposed in addition to the focal length changing optical system 70.

Figure 16:
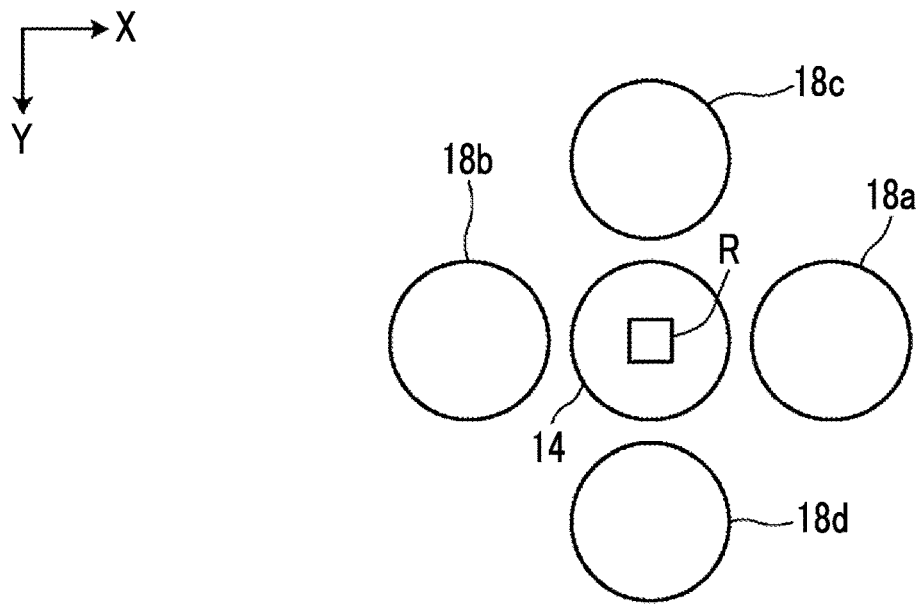
FIG. 16 is a diagram showing a modification example in which four displacement sensors are provided in the observation device according to the embodiment of the present disclosure.

Further, in the above embodiment, the first auto-focus displacement sensor 18a and the second auto-focus displacement sensor 18b are provided side by side in the X direction with the phase difference lens 14a being interposed therebetween, but as shown in FIG. 16, a third auto-focus displacement sensor 18c and a fourth auto-focus displacement sensor 18d may be provided side by side in the Y direction with the phase difference lens 14a being interposed therebetween.

Figure 17:
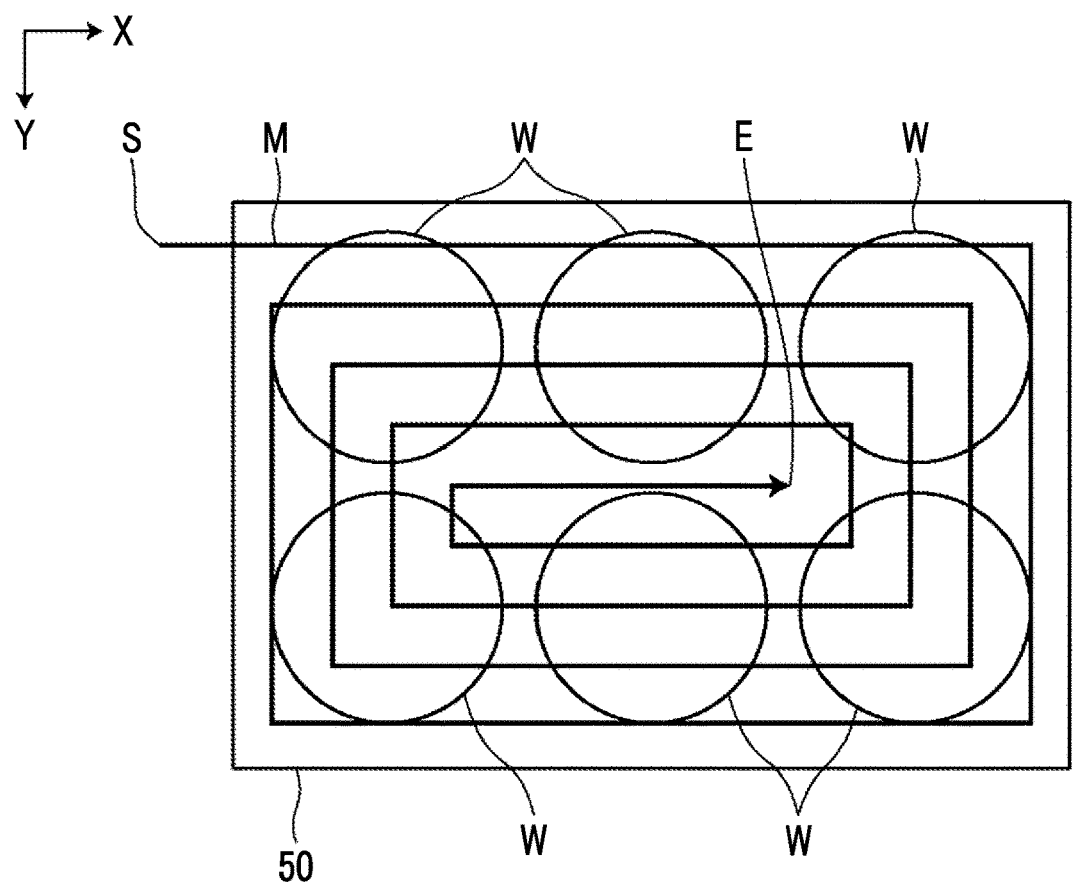
FIG. 17 is a diagram showing another example of the scanning position depending on an observation region in the culture container.

Thus, it is possible to reciprocating the observation region R, and also, to move the observation region R as shown in FIG. 17. That is, in FIG. 17, the observation region R is moved from the scanning start point S in a positive direction (a rightward direction in FIG. 17) in the X direction, is moved in a positive direction (a downward direction in FIG. 17) in the Y direction, is moved in a negative direction (in a leftward direction in FIG. 17) in the X direction, and then, is moved in a negative direction (an upward direction in FIG. 17) in the Y direction. Thus, it is possible to scan the inside of the culture container 50 in a two-dimensional manner by repeatedly moving the observation region R in the X direction and the Y direction. In this case, it is possible to detect a boundary portion between wells by the third and fourth auto-focus displacement sensors 18c and 18d, in addition to the first and second auto-focus displacement sensors 18a and 18b.

Further, in the above-described embodiment, the present disclosure is applied to the phase difference microscope, but the present disclosure is not limited to the phase difference microscope, and may be applied to a different microscope such as a differential interference microscope or a bright field microscope.

In addition, in the above-described embodiments, a configuration in which a phase difference image formed by the imaging optical system 14 is captured by the imaging element 16 is shown, but a configuration in which an imaging element is not provided and an observation optical system or the like is provided so that a user is able to directly observe a phase difference image of an observation target formed by the imaging optical system 14 may be used. In this case, the observation device may be provided with at least one operation section among the first operation section 15A, the second operation section 15B, the fourth operation section 15D, and the sixth to seventh operation sections 15F and 15G to perform the auto-focus control. In this case, the fifth operation section 15E may be further provided to perform the auto-focus control. Further, instead of the focal length changing optical system 70 and the seventh operation section 15G, the focal length changing optical system 75 and the eighth operation section 15H may be provided to perform the auto-focus control.

What is claimed is:

1. An observation device comprising:
an imaging optical system having an imaging lens that forms an image of an observation target in a plurality of containers in which the observation target is contained;
an imaging system having an imaging element that captures the image of the observation target formed by the imaging optical system;
an operation section that performs at least one of a first operation of changing a focal length of the imaging optical system, a second operation of moving the imaging lens in an optical axis direction, a third operation of moving the imaging element in the optical axis direction, or a fourth operation of moving the container in the optical axis direction;
a horizontal driving section that moves at least one of the container or the imaging optical system in a horizontal plane;
a scanning controller that controls the horizontal driving section and moves at least one of the container or the imaging optical system to scan an observation position in the container;
an auto-focus controller that controls the operation section and performs an auto-focus control for each observation position; and
a detection section that precedently detects a vertical position of the container at each observation position before the imaging optical system reaches the observation position,
wherein the auto-focus controller switches a start timing of the auto-focus control for each observation position, on the basis of a boundary portion between the adjacent containers in a scanning direction of the observation position,
wherein the auto-focus controller performs the auto-focus control for each observation position on the basis of a detection signal of the detection section, and
wherein the detection section includes at least two displacement sensors that are provided in parallel in the scanning direction with the imaging optical system being interposed therebetween, and a displacement sensor to be used is switched according to a directional change of the scanning direction.

2. The observation device according to claim 1,
wherein the operation section performs a plurality of operations among the first operation, the second operation, the third operation, and the fourth operation.

3. The observation device according to claim 1,
wherein the imaging optical system further includes an objective lens that forms the image of the observation target in the container, and
wherein the first operation includes at least one of an operation of changing a focal length of the imaging lens or an operation of changing a focal length of the objective lens.

4. The observation device according to claim 3,
wherein the operation section performs a fifth operation of moving the objective lens in the optical axis direction.

5. The observation device according to claim 1, further comprising:
a focal length changing optical system that changes the focal length of the imaging optical system,
wherein the imaging optical system further includes an objective lens that forms the image of the observation target in the container, and
wherein the first operation includes at least one of an operation of changing a focal length of the imaging lens, an operation of changing a focal length of the objective lens, or an operation of changing the focal length of the imaging optical system by the focal length changing optical system.

6. The observation device according to claim 1, further comprising:
a focal length changing optical system that changes the focal length of the imaging optical system,
wherein the first operation includes an operation of changing the focal length of the imaging optical system by the focal length changing optical system.

7. The observation device according to claim 1,
wherein the imaging optical system further includes an objective lens that forms the image of the observation target in the container, and
wherein the operation section performs a fifth operation of moving the objective lens in the optical axis direction.

8. The observation device according to claim 1,
wherein the auto-focus controller starts the auto-focus control of the observation position immediately after the boundary portion from a time point when the auto-focus control of the observation position immediately before the boundary portion is terminated until before the imaging optical system reaches the observation position immediately after the boundary portion.

9. The observation device according to claim 8,
wherein the auto-focus controller starts, for an observation position other than the observation position immediately after the boundary portion, the auto-focus control from a time point when the imaging optical system reaches the observation position.

10. The observation device according to claim 8,
wherein a time for the auto-focus control of the observation position immediately after the boundary portion is longer than a time for the auto-focus control of the observation position other than the observation position immediately after the boundary portion.

11. The observation device according to claim 8,
wherein a time for the auto-focus control of the observation position immediately after the boundary portion is longer than a time for the auto-focus control of the observation position other than the observation position immediately after the boundary portion.

12. The observation device according to claim 1,
wherein the detection section detects a boundary portion of the container.

13. The observation device according to claim 1,
wherein the auto-focus controller performs, in a case where the detection signal detected by the detection section is abnormal, for an observation position where the abnormal detection signal is detected, the auto-focus control based on the detection signals of the detection section observation positions before and after the observation position in the scanning direction.

14. The observation device according to claim 1, further comprising:
a storage unit that stores position information of a boundary portion of the container,
wherein the auto-focus controller switches a start timing of the auto-focus control on the basis of the position information of the boundary portion stored in the storage unit.

15. The observation device according to claim 1,
wherein the container is each well of a well plate.

16. An observation device comprising:
- an imaging optical system having an imaging lens that forms an image of an observation target in a plurality of containers in which the observation target is contained;
- an operation section that performs at least one of a first operation of changing a focal length of the imaging optical system, a second operation of moving the imaging lens in an optical axis direction, or a fourth operation of moving the container in the optical axis direction;
- a horizontal driving section that moves at least one of the container or the imaging optical system in a horizontal plane;
- a scanning controller that controls the horizontal driving section and moves at least one of the container or the imaging optical system to scan an observation position in the container;
- an auto-focus controller that controls the operation section and performs an auto-focus control for each observation position; and
- a detection section that precedently detects a vertical position of the container at the observation position before the imaging optical system reaches the observation position,
- wherein the auto-focus controller switches a start timing of the auto-focus control for each observation position, on the basis of a boundary portion between the adjacent containers in a scanning direction of the observation position,
- wherein the auto-focus controller performs the auto-focus control for each observation position on the basis of a detection signal of the detection section, and
- wherein the detection section includes at least two displacement sensors that are provided in parallel in the scanning direction with the imaging optical system being interposed therebetween, and the displacement sensor to be used is switched according to a directional change of the scanning direction.

17. The observation device according to claim 16, wherein the operation section performs a plurality of operations among the first operation, the second operation, and the fourth operation.

18. The observation device according to claim 16,
- wherein the imaging optical system further includes an objective lens that forms the image of the observation target in the container, and
- wherein the first operation includes at least one of an operation of changing a focal length of the imaging lens or an operation of changing a focal length of the objective lens.

19. The observation device according to claim 16, further comprising:
- a focal length changing optical system that changes the focal length of the imaging optical system,
- wherein the imaging optical system further includes an objective lens that forms the image of the observation target in the container, and
- wherein the first operation includes at least one of an operation of changing a focal length of the imaging lens, an operation of changing a focal length of the objective lens, or an operation of changing the focal length of the imaging optical system by the focal length changing optical system.

20. The observation device according to claim 19, wherein the operation section performs a fifth operation of moving the objective lens in the optical axis direction.

21. The observation device according to claim 16, further comprising:
- a focal length changing optical system that changes the focal length of the imaging optical system,
- wherein the first operation includes an operation of changing the focal length of the imaging optical system by the focal length changing optical system.

22. The observation device according to claim 16,
- wherein the imaging optical system further includes an objective lens that forms the image of the observation target in the container, and
- wherein the operation section performs a fifth operation of moving the objective lens in the optical axis direction.

23. The observation device according to claim 16,
- wherein the auto-focus controller starts the auto-focus control of the observation position immediately after the boundary portion from a time point when the auto-focus control of the observation position immediately before the boundary portion is terminated until before the imaging optical system reaches the observation position immediately after the boundary portion.

24. The observation device according to claim 23,
- wherein the auto-focus controller starts, for an observation position other than the observation position immediately after the boundary portion, the auto-focus control from a time point when the imaging optical system reaches the observation position.

25. The observation device according to claim 16,
- wherein the detection section detects a boundary portion of the container.

26. The observation device according to claim 16,
- wherein the auto-focus controller performs, in a case where the detection signal detected by the detection section is abnormal, for an observation position where the abnormal detection signal is detected, the auto-focus control based on the detection signals of the detection section observation positions before and after the observation position in the scanning direction.

27. The observation device according to claim 16, further comprising:
- a storage unit that stores position information of a boundary portion of the container,
- wherein the auto-focus controller switches a start timing of the auto-focus control on the basis of the position information of the boundary portion stored in the storage unit.

28. The observation device according to claim 16,
- wherein the container is each well of a well plate.

29. An observation method for moving at least one of a plurality of containers in which an observation target is contained, or an imaging optical system having an imaging lens that forms an image of the observation target in each of the containers, to scan each observation position in the container in an observation region of the imaging optical system and capture an image of the observation target imaged by the imaging optical system using an imaging element, the method comprising:
- changing a focal length of the imaging optical system, moving the imaging lens in an optical axis direction, moving the imaging element in the optical axis direction, moving the container in the optical axis direction, or any combination thereof;
- switching a start timing of an auto-focus control for each observation position, on the basis of a boundary portion between the adjacent containers in a scanning direction of the observation position;

precedently detecting a vertical position of the container at each observation position before the imaging optical system reaches the observation position; and performing the auto-focus control for each observation position on the basis of a detection signal indicating the vertical position of the container at each observation position, wherein the vertical position of the container at each observation position is detected by at least two displacement sensors that are provided in parallel in the scanning direction with the imaging optical system being interposed therebetween, and a displacement sensor to be used is switched according to a directional change of the scanning direction.

30. A non-transitory computer-readable recording medium having stored therein an observation device control program that causes a computer to execute an observation method for moving at least one of a plurality of containers in which an observation target is contained, or an imaging optical system having an imaging lens that forms an image of the observation target in each of the containers, to scan each observation position in the container in an observation region of the imaging optical system and capture an image of the observation target imaged by the imaging optical system using an imaging element, the program being executable by the computer to perform processing comprising:

changing a focal length of the imaging optical system, moving the imaging lens in an optical axis direction, moving the imaging element in the optical axis direction, moving the container in the optical axis direction, or any combination thereof;

switching a start timing of an auto-focus control for each observation position, on the basis of a boundary portion between the adjacent containers in a scanning direction of the observation position;

precedently detecting a vertical position of the container at each observation position before the imaging optical system reaches the observation position; and performing the auto-focus control for each observation position on the basis of a detection signal indicating the vertical position of the container at each observation position, wherein the vertical position of the container at each observation position is detected by at least two displacement sensors that are provided in parallel in the scanning direction with the imaging optical system being interposed therebetween, and a displacement sensor to be used is switched according to a directional change of the scanning direction.

31. An observation device comprising:

an imaging optical system having an imaging lens that forms an image of an observation target in a plurality of containers in which the observation target is contained;

an imaging system having an imaging element that captures the image of the observation target formed by the imaging optical system;

an operation section that performs at least one of a first operation of changing a focal length of the imaging optical system, a second operation of moving the imaging lens in an optical axis direction, a third operation of moving the imaging element in the optical axis direction, or a fourth operation of moving the container in the optical axis direction;

a horizontal driving section that moves at least one of the container or the imaging optical system in a horizontal plane;

a scanning controller that controls the horizontal driving section and moves at least one of the container or the imaging optical system to scan an observation position in the container;

an auto-focus controller that controls the operation section and performs an auto-focus control for each observation position; and a detection section that precedently detects a vertical position of the container at each observation position before the imaging optical system reaches the observation position, wherein the auto-focus controller switches a start timing of the auto-focus control for each observation position, on the basis of a boundary portion between the adjacent containers in a scanning direction of the observation position, wherein the auto-focus controller performs the auto-focus control for each observation position on the basis of a detection signal of the detection section, and wherein the auto-focus controller performs the auto-focus control, in a case where the detection signal detected by the detection section is abnormal, for an observation position where the abnormal detection signal is detected, based on the detection signals of the detection section indicating observation positions before and after the observation position in the scanning direction.

32. An observation method for moving at least one of a plurality of containers in which an observation target is contained, or an imaging optical system having an imaging lens that forms an image of the observation target in each of the containers, to scan each observation position in the container in an observation region of the imaging optical system and capture an image of the observation target imaged by the imaging optical system using an imaging element, the method comprising:

changing a focal length of the imaging optical system, moving the imaging lens in an optical axis direction, moving the imaging element in the optical axis direction, moving the container in the optical axis direction, or any combination thereof;

switching a start timing of an auto-focus control for each observation position, on the basis of a boundary portion between the adjacent containers in a scanning direction of the observation position;

precedently detecting a vertical position of the container at each observation position before the imaging optical system reaches the observation position;

performing the auto-focus control for each observation position on the basis of a detection signal indicating the vertical position of the container at each observation position; and performing the auto-focus control, in a case where the detection signal detected by the detection section is abnormal, for an observation position where the abnormal detection signal is detected, based on detection signals indicating observation positions before and after the observation position in the scanning direction.

33. A non-transitory computer-readable recording medium having stored therein an observation device control program that causes a computer to execute an observation method for moving at least one of a plurality of containers in which an observation target is contained, or an imaging optical system having an imaging lens that forms an image of the observation target in each of the containers, to scan each observation position in the container in an observation region of the imaging optical system and capture an image of the observation target imaged by the imaging optical system using an imaging element, the program being executable by the computer to perform processing comprising:

changing a focal length of the imaging optical system, moving the imaging lens in an optical axis direction, moving the imaging element in the optical axis direction, moving the container in the optical axis direction, or any combination thereof;

switching a start timing of an auto-focus control for each observation position, on the basis of a boundary portion between the adjacent containers in a scanning direction of the observation position;

precedently detecting a vertical position of the container at each observation position before the imaging optical system reaches the observation position;

performing the auto-focus control for each observation position on the basis of a detection signal indicating the vertical position of the container at each observation position; and performing the auto-focus control, in a case where the detection signal detected by the detection section is abnormal, for an observation position where the abnormal detection signal is detected, based on detection signals indicating observation positions before and after the observation position in the scanning direction.

34. An observation device comprising:

an imaging optical system having an imaging lens that forms an image of an observation target in a plurality of containers in which the observation target is contained;

an operation section that performs at least one of a first operation of changing a focal length of the imaging optical system, a second operation of moving the imaging lens in an optical axis direction, or a fourth operation of moving the container in the optical axis direction;

a horizontal driving section that moves at least one of the container or the imaging optical system in a horizontal plane;

a scanning controller that controls the horizontal driving section and moves at least one of the container or the imaging optical system to scan an observation position in the container;

an auto-focus controller that controls the operation section and performs an auto-focus control for each observation position; and a detection section that precedently detects a vertical position of the container at the observation position before the imaging optical system reaches the observation position, wherein the auto-focus controller switches a start timing of the auto-focus control for each observation position, on the basis of a boundary portion between the adjacent containers in a scanning direction of the observation position;

wherein the auto-focus controller performs the auto-focus control for each observation position on the basis of a detection signal of the detection section, and wherein the auto-focus controller performs the auto-focus control, in a case where the detection signal detected by the detection section is abnormal, for an observation position where the abnormal detection signal is detected, based on the detection signals of the detection section observation positions before and after the observation position in the scanning direction.

* * * * *